US006299742B1

(12) United States Patent
Pal et al.

(10) Patent No.: US 6,299,742 B1
(45) Date of Patent: Oct. 9, 2001

(54) APPARATUS FOR METAL EXTRACTION

(75) Inventors: Uday Pal, Dover, MA (US); Stephen C. Britten, Ansonia, CT (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 09/368,308

(22) Filed: Aug. 3, 1999

Related U.S. Application Data

(62) Division of application No. 09/002,581, filed on Jan. 5, 1998, now Pat. No. 5,976,345.
(60) Provisional application No. 60/034,687, filed on Jan. 6, 1997.

(51) Int. Cl.[7] .................................................. B01D 59/40
(52) U.S. Cl. ...................... 204/243.1; 205/336; 205/368; 205/369; 205/370; 205/371; 205/398; 205/400; 205/404; 205/367
(58) Field of Search .................................. 205/369, 370, 205/371, 398, 400, 401, 404, 410, 367, 368, 336; 204/243.1, 244, 247

(56) References Cited

U.S. PATENT DOCUMENTS

| | | | |
|---|---|---|---|
| 3,562,135 | 2/1971 | Marincek | 204/243 |
| 3,692,645 | 9/1972 | Marincek | 204/67 |
| 4,108,743 | * 8/1978 | Minck | 204/64 R |
| 4,804,448 | 2/1989 | Sammells et al. | 204/243 R |
| 4,865,925 | 9/1989 | Ludwig et al. | 429/12 |
| 4,908,113 | 3/1990 | Marianowski et al. | 204/243 R |
| 4,995,948 | * 2/1991 | Poa et al. | 204/1.5 |
| 5,089,094 | 2/1992 | Ogasawara et al. | 204/70 |
| 5,312,525 | 5/1994 | Pal et al. | 204/64 R |
| 5,380,467 | 1/1995 | Lin et al. | 252/520 |
| 5,567,286 | 10/1996 | Pal et al. | 204/246 |

FOREIGN PATENT DOCUMENTS 1948462  4/1971  (DE).

OTHER PUBLICATIONS

W.C. Maskall, "Inorganic Solid State Chemically Sensitive Devices" Electrochemical Oxygen Gas Sensors *J. Phys. E: Sci. Instrum.* 20:1156 (Oct. 1987).
Nisancioglu et al., "Potentiostatic Step Technique to Study Ionic Transport in Mixed Conductors" *Solid States Ionics* 72:199 (1994), No month given.
Iwase et al., "Electronically Driven Transport of Oxygen from Liquid Iron to CO = $CO_2$ Gase Mixtures Through Stabilized Zirconia" *Metallurgical Transactions B* 12B:517 (Sep. 1981).

* cited by examiner

Primary Examiner—Kathryn Gorgos
Assistant Examiner—Thomas H Parsons
(74) Attorney, Agent, or Firm—Hale and Dorr LLP

(57) ABSTRACT

An amperometric in situ apparatus and technique for measuring the concentrations and transport properties of easily dissociable oxides in slags is described. The technique consists of a combination of different measurements utilizing an electrolyte to separate a reference-gas compartment from the slag of interest. A method and apparatus for metals extraction is also described which includes a vessel for holding a molten electrolyte, the electrolyte comprising a mobile metallic species and an anionic species having a diffusivity greater than about $10^{-5}$ cm$^2$/sec; a cathode and an anode, the cathode in electrical contact with the molten metal electrolyte, the cathode and molten electrolyte separated from the anode by an ionic membrane capable of transporting the anionic species of the electrolyte into the membrane; and a power source for generating a potential between the cathode and the anode.

22 Claims, 14 Drawing Sheets

APPARATUS FOR METAL EXTRACTION

CROSS-REFERENCE TO RELATED APPLICATIONS

This application is a divisional of U.S. patent application Ser. No. 09/002,581 filed Jan. 5, 1998, now issued as U.S. Pat. No. 5,976,345. This application further claims the benefit of U.S. Provisional Patent Application No. 60/034,687 filed Jan. 6, 1997.

BACKGROUND OF THE INVENTION

1. Field of the Invention

This invention relates to a process and apparatus for the electrochemical extraction of metals dissolved in a molten electrolyte. The invention further relates to an apparatus for determining the metal composition, oxidation state of the metal species and their transport properties in a melt such as oxide and other slags in metallurgical reactors and various types of molten glasses.

2. Description of the Related Art

The extraction of metals from ores can be accomplished by pyrometallurgical or electrochemical means. Smelting is the predominant method of pyrometallurgical refining. In smelting, the ore is heated with a reducing agent and a flux to a high temperature. The reducing agent typically combines with the oxygen in the ore, yielding a pure metal or alloy and solid, liquid or gaseous oxide byproducts. The flux reacts with the oxide byproducts and with the unreacted components of the ore to form a liquid slag at the smelting temperature. Slag also refines the metal by incorporating one or more impurities. The slag can be physically separated from the refined metal. Smelting processes are used to extract iron, nickel, copper, lead, etc. from their ores. More metal is refined by smelting than by any other refining technique.

Electrolysis is the most common form of electrochemical refining. In an electrolysis process, the ore is dissolved in an aqueous or non-aqueous solution or melted in an electrolytic furnace. Once dissolved or melted, the ore dissociates into ionic species, forming an electrolyte. The metallic components of the ore to be extracted become positively charged cations. The remaining components, typically oxygen, carbonate, sulfate, chloride or fluoride become negatively charged anions. To extract the metal from the ore, an electric potential is applied across two electrodes which are immersed in the electrolyte. The metallic ions are thereby attracted to the negatively charged cathode, where they combine with electrons and are deposited as metal. The oxygen, sulfate, carbonate, chloride or fluoride ions are driven to the positively charged anode and evolve as waste gases. Aluminum, calcium, magnesium, and beryllium are examples of metals refined by electrochemical processes. Whereas electrochemical processes are usually preferred compared to pyrometallurgical processes, for quick energy efficient extraction and refining of metals, material selection for the electrolyte and process apparatus prevents broader application. They are usually restricted to the extraction of metals whose ores form very stable compounds.

Pal et al. in U.S. Pat. No. 5,567,286 describes a method for the electrochemical recovery of metals from slag using a galvanic (current producing) cell in which no external electric potential is applied. The refining process is driven by the chemical-potential gradient between the oxygen concentration within the slag and a refining gas which is separated from the slag by a solid electrolyte; however, because the chemical-potential gradient is fixed by the refining gas, the cell is not well suited for extracting on an industrial scale the desired metal from a melt that contains different metals.

Sammells et al. describe a cell for the formation of lithium metal and oxygen from molten metal salts containing lithium oxide, in which a cathode is immersed in a molten-salt electrolyte separated from an anode by a solid electrolyte. Sammells et al. rely upon high lithium cation mobility in order to drive the electrolysis reaction. The process as described by Sammells et al. requires suitable alkali ion conducting molten salt electrolyte having high alkali ion conductivity and thereby discourages applications involving transition metal and other cations with mobilities less than that of lithium. Also, the solid electrolyte used by Sammells et al is unsuitable for operation at higher temperatures because the solid zirconia-based electrolyte becomes partially electronic at high temperatures and short-circuits the cell, thereby reducing the efficiency of the cell.

Driven by the ever-rising demand for metals and the increasing scarcity of available mineral resources, there exists a need for an energy efficient, environmentally benign process for the refining of ores. Conventional electrolysis processes fail to meet these needs in that (1) the process is slowed by charge build up or polarization at the electrodes, (2) the electrolysis cell can get electrically shorted because the cathode and anode are both in the cell, (3) when refining metals with multiple or variable valencies parasitic reactions may occur at the anode and decrease the efficiency of the cell, and (4) product formation at the anode increases cell resistance.

Thus, there remains a need for a process and apparatus which will allow metals including non-reactive metals and metals with variable valencies, i.e., metals having more than one oxidation state, to be extracted from their respective ores via an electrolytic process that is environmentally sound and economically viable.

Sensors for the determination of oxygen concentration have been used extensively in the steelmaking process for better control of deoxidation, continuous casting, and ingot-making processes (see, Iwase et al. "Electronically Driven Transport of Oxygen from Liquid Iron to $CO+CO_2$ Gas Mixtures Through Stabilized Zirconia" *Metallurgical Transactions* B 12B:517 (Sept. 1981)). Potentiometric sensors based on open-circuit techniques utilizing a metal/metal oxide reference are used extensively in the steel industry. These open-circuit measurements can give steelmakers an accurate evaluation of the oxygen activity and even the $FeO_x$ activity within a slag. However, potentiometric sensors can neither determine the actual concentration of $FeO_x$ nor provide information concerning the kinetics associated with diffusion within the slag. Also, slags with drastically different $FeO_x$ concentrations may have identical oxygen potentials, depending upon the structure and properties of the rest of the slag. Meanwhile the diffusion of $FeO_x$ species within the slag will be strongly dependent upon the intrinsic slag structure, basicity, and viscosity—none of which are directly measured in any way by the potentiostatic method. These variables are important because it is often the kinetics and not the thermodynamics which are important in controlling the slag/metal reactions of interest to steelmakers.

In addition to the information of oxygen activity provided by conventional oxygen sensors, there remains a need for rapid and accurate determination of the actual concentration and transport properties of metallic species in the slag. The importance of such information to the metals processing industry cannot be overestimated. Chemical analyses for FeO$_x$ in situ would allow steelmakers to control the slag chemistry by adding suitable fluxes thereby lowering the inclusion content of the steel, and information on the transport properties would allow the steelmakers to enhance the kinetics of the steelmaking process.

It is an object of the present invention to provide a method and apparatus for the extraction of metal from a metal-containing electrolyte which overcomes the deficiencies of the prior art.

It is a further object of the present invention to provide a method and apparatus for the extraction of metal from a metal-containing electrolyte which electronically separates the anode and the cathode.

It is another object of the present invention to provide a method and apparatus for the extraction of metal from a metal-containing electrolyte which is highly efficient, versatile, suitable for industrial scale processing and which may be used in the processing of a wide range of metals.

It is yet another object of the present invention to provide a method and apparatus for the determination of metallic species composition and transport properties in a metal-containing electrolyte.

These and other objectives of the present invention are achieved by practice of the present invention.

SUMMARY OF THE INVENTION

In one aspect of the invention, an apparatus for metal extraction is provided, which includes a vessel for holding a molten electrolyte, the electrolyte comprising mobile metallic species and anionic species having an ionic conductivity greater than 0.001 $(\Omega\text{-cm})^{-1}$, the metallic species being reduced for metal extraction not needing to have high mobility, a cathode and an anode and a power source for generating a potential between the cathode and the anode. It is preferred that the metallic species being reduced have a mobility as measured by a transport number less than 0.9. It is also preferred that the ionic conductivity of the anionic species be greater than 0.1 $(\Omega\text{-cm})^{-1}$. The cathode is in electrical contact with a molten electrolyte, and the cathode and molten electrolyte are separated from the anode by an ionic membrane capable of transporting the anionic species of the electrolyte into the membrane.

In yet another aspect of the present invention, an apparatus for determining metallic species composition and transport properties in a molten electrolyte such as an oxide slag is provided which includes a vessel for receiving a molten electrolyte whose metal content and oxidation state along with its transport properties are to be measured; a cathode and an anode, the cathode in electrical contact with a molten electrolyte, the cathode and molten electrolyte separated from the anode by a solid ionic membrane capable of transporting an anionic species associated with the metal of the electrolyte into the membrane, the anode in contact with the solid electrolyte membrane and a reference gas; a first reference electrode (RE1), positioned in electrical contact with the solid electrolyte membrane so as to be capable of measuring a potential at a membrane-reference gas interface; a second reference electrode (RE2), positioned in electrical contact with the cathode so as to be capable of measuring a potential at the molten electrolyte-cathode interface; a power source for generating a potential between the cathode and the anode; and means for measuring the potential difference between the first and second reference electrodes.

In one embodiment of the apparatus for metal extraction, the ionic membrane is comprised of a primary membrane in contact with the molten electrolyte and a secondary membrane adjacent thereto and having substantially only ionic conducting characteristics. In preferred embodiments, the molten electrolyte is at a temperature greater than about 400° C., and preferably in the range of about 1000° C.–2000° C., and most preferably about 1200° C.–1600° C. In other preferred embodiments, the primary membrane possesses primarily ionic conducting characteristics under use conditions.

In other preferred embodiments, the ionic membrane comprises a solid membrane. The solid electrolyte comprises a refractory metal oxide, such as partially-stabilized zirconia (PSZ), or other inorganic solid electrolytes, such as calcium sulfide. The ionic membrane may comprise an immiscible liquid electrolyte. A secondary ionic membrane may be included adjacent to the primary solid membrane, such as CaAlSiFeO$_x$, where x is selected to provide a molten metal oxide possessing high ionic conductivity and little or no electronic conductivity. The vessel or at least a portion of the vessel for holding the molten electrolyte may be comprised of the solid-electrolyte membrane. It may be noted that the primary membrane or the primary-secondary membrane combination when used must have an ionic conductivity greater than 0.001 $(\Omega\text{-cm})^{-1}$ and preferably greater than 0.1 $(\Omega\text{-cm})^{-1}$.

In other preferred embodiments, the anode is in contact with the ionic membrane. The apparatus may include means for removing gaseous reactant products at the anode.

In another preferred embodiment, the apparatus for refining a metal may additionally include a first reference electrode positioned in electrical contact with the cathode so as to be capable of measuring a potential at the molten electrolyte-cathode interface, a second reference electrode positioned in electrical contact with the ionic membrane so as to be capable of measuring a potential at the membrane-air or reference gas interface, and means for measuring a potential between the first or second reference electrodes.

In another preferred embodiment, the electrolyte may contain transition metals, main group metals, alkaline earth elements, alkali metals, or rare earth elements. The electrolyte may comprise MeX, where Me is one or more metallic species selected from the group consisting of gold (Au), silver (Ag), nickel (Ni), cadmium (Cd), cobalt (Co), tungsten (W), tin (Sn), vanadium (V), zinc (Zn), chromium (Cr), copper (Cu), lead (Pb), iron (Fe), molybdenum (Mo), silicon (Si), magnesium (Mg), manganese (Mn), boron (B) and titanium (Ti), and where X is an anionic species selected from the group consisting of oxide, sulfide, halide and combinations thereof. The molten electrolyte may be metal oxide slag.

In one embodiment of the invention, the power source is capable of applying a potential selected to electrolytically reduce the metallic species of the molten metal electrolyte to the corresponding metal. The potential may be selected so as to selectively reduce a single species or two or more metallic species at a time. The apparatus may include a plurality of cathode and anode electrolytic cells, each cell capable of independently applying a potential.

In yet another embodiment of the invention, the apparatus for determining composition of a metallic species, further includes means adapted to receive electrical input signals and to transmit an output signal characteristic of the molten electrolyte composition and transport properties, such as current-time and/or i-V plots. The power source may apply a potential sweep or a step potential.

In yet another aspect of the invention, a metallic species' composition and transport properties in molten electrolytes such as a slag may be determined by generating a potential between a cathode and an anode, the cathode in electrical contact with a molten metal electrolyte comprising metallic species to be measured, the cathode and molten metal electrolyte separated from the anode by an ionic membrane capable of transporting an anion associated with the metallic species across the membrane, whereby a current is generated; and monitoring the resulting current-potential profile utilizing reference electrodes at the reference gas-ionic membrane interface and molten electrolyte-cathode interface.

In yet another aspect of the invention, a metal may be extracted from a molten electrolyte by providing a cathode and an anode, the cathode in electrical contact with a molten electrolyte, the molten electrolyte comprising a mobile metallic species and a mobile anionic species, the cathode and molten electrolyte separated from the anode by an ionic membrane capable of transporting the anionic species of the electrolyte across the membrane, and generating a potential between the cathode and the anode, the potential selected to reduce the metallic species of the electrolyte, whereby the anionic species of the electrolyte is transported across the ionic membrane and is oxidized at the anode. The potential may be selected to reduce a single metallic species or two or more metallic species simultaneously.

"Molten electrolyte", as that term is used herein, means a material which is ionic and contains metallic cations (positively charged) and anionic counterions (negatively charged). The electrolyte is typically a metal oxide melt or slag (vitreous material formed on the surface of more dense molten metals or below the surface of less dense molten metal which includes a variety of metal oxides), but it may also include other metal compounds such as metal sulfides, metal chlorides, metal fluorides, etc. The ionic transport number of the metallic species being reduced can be as low as 0.01, i.e., the metallic species being reduced can have low mobility or carry as little as 1% of the total charge.

The "solid electrolyte membrane", "ionic membrane", "liquid electrolyte membrane" and the like, as those terms are used herein, mean a substantially non-porous ionic membrane selected such that its ionically conductive species are the same as the anionic species of the molten electrolyte. Additionally the membrane is desirably a refractory material and is desirably highly resistant to corrosion which may occur at the high temperatures used in these molten oxide systems. An oxygen conducting solid electrolyte membrane is typically used for molten metal oxide electrolytes, such as by way of example only, but not restricted to, zirconia and rare earth element-stabilized or partially-stabilized derivatives thereof.

By "ionic character", as that term is used herein, it is meant the ability of an electrolyte to transport an ionic species into and/or through an electrolytic medium. It is desired that the conductivity of the electrolyte be greater than $0.001(\Omega\text{-cm})^{-1}$, and preferably about $0.1\ (\Omega\text{-cm})^{-1}$. It is further preferred that about at least 90% of the electrolyte conductivity is due to ionic conduction (i.e., the sum of the transport numbers of the individual ionic species must be at least 0.9).

By "electronic character", as that term is used herein, it is meant the ability of an electrolyte to conduct or transport electrons through an electrolyte medium.

By "ion mobility", as that term is used herein, it is meant the ability of an ion to move under the influence of an electric field.

By "diffusivity", as that term is used herein, is the measure of the rate of diffusion or transport of a particular species, e.g., an anion, within a solution, herein a molten electrolyte.

The present invention is useful in extraction of high purity metals and/or alloys and/or metal compounds from their respective ores. It may also be useful in electrolytic recycling of waste oxide slags and fluxes utilized in conventional metals processing. It may also be used to determine metallic species composition and transport properties in molten metal electrolytes such as a slag. This information can be used to improve product quality and to enhance process kinetics of existing metal production processes, as well as the new electrochemical extraction of metals and alloys.

BRIEF DESCRIPTION OF THE DRAWING

The invention is understood with reference to the figures, which are presented for the purpose of illustration only and are in no way limiting of the invention and in which.

DETAILED DESCRIPTION OF THE INVENTION

The process and apparatus described herein permit a broad family of metals, including non-reactive metals and metals with multiple oxidation states, to be extracted from their respective ores via an electrolytic process that is environmentally sound and economically viable. The apparatus and method of the invention also may be adapted for use as a sensor for determination of metal composition, oxidation states and transport properties.

Metal Extraction Method and Apparatus

Figure 1:
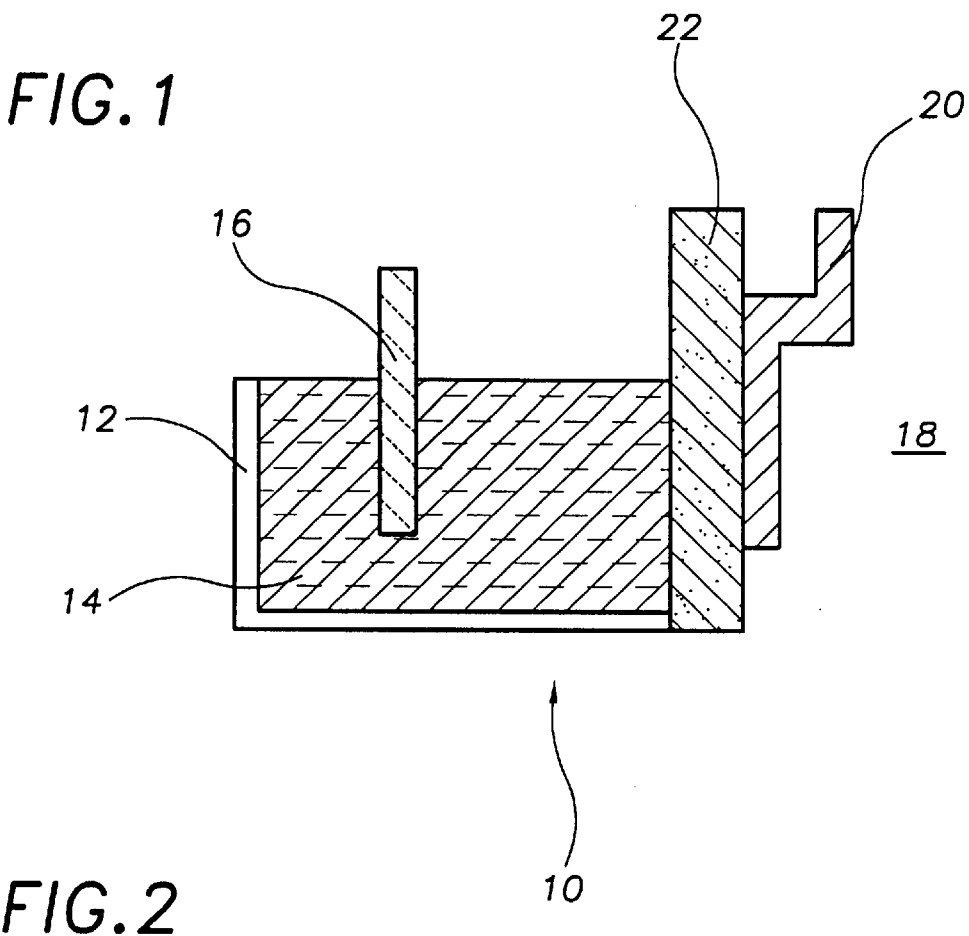
FIG. 1 is a schematic illustration of an electrolysis cell of the invention.

With reference to FIG. 1, the apparatus 10 in its most general embodiment includes a vessel 12 for holding a metal-containing electrolyte 14. At elevated temperatures, the molten electrolyte contains both mobile metallic (cationic) species and anionic species having an ionic conductivity greater than about 0.001 $(\Omega\text{-cm})^{-1}$, and preferably greater than 0.1 $(\Omega\text{-cm})^{-1}$. These values for the molten electrolyte are established by adjusting the variable valence cations. The ionic transport number of the metallic species being reduced can be as low as 0.01, i.e., the metallic species being reduced can have low mobility or carry as little as 1% of the total charge. One or more cathodes 16 in electrical contact with the metal-containing electrolyte are separated from a reference gas 18 and an anode 20 by one or more ionic membranes 22. The ionic membrane or its combination is selected for its highly ionic character. Desirably, the ionic membrane is a purely ionic transport conductor capable of conducting the anionic species associated with the metallic species to be recovered.

An electrochemical potential is established across the molten electrolyte and the membrane by applying a potential across electrodes 16, 20, where the cathode 16 is in contact with the metal-containing electrolyte and the anode 20 may be located at the interface of the ionic membrane and the reference gas. The electrochemical potential gradient is easily established and may be controlled electrically (by control of the applied potential) such that the desired metallic species of the metal-containing electrolyte is reduced at the cathode. The anion migrates (diffuses) from the molten electrolyte and through the ionic membrane and is oxidized at the anode. The oxidation product is typically a gas, e.g., $O_2$, which can be readily removed from the anode region. The half-reactions of the cell are generally depicted as:

$$Me^{n+} + ne^- \rightarrow Me° \quad \text{(cathode)} \qquad \text{eq}(1)$$

$$X^{m-} \rightarrow X° + me^-, \quad \text{(anode)} \qquad \text{eq}(2)$$

where Me is the metallic species; X is the anionic species, and m,n are associated with the valence of the species.

Where the diffusivity of the anion is greater than $10^{-5}$ cm$^2$/sec, transport of the anion through the electrolyte and to the ionic membrane is not rate limiting. Thus, no charge gradient develops at the molten electrolyte/ionic membrane interface, which would reduce the electrolysis rate over time. The charge gradient at the molten electrolyte/ionic membrane interface can also be eliminated by increasing the molten electrolyte/ionic membrane interfacial area. The apparatus therefore is not restricted to operation at the triple point (cathode/electrode/solid membrane interface), but takes place at the entire cathode/electrolyte interface, which is very helpful in scale-up of the operation. The triple point is an arrangement of elements in the apparatus in which the cathode, molten electrolyte and ionic membrane are in contact with each other at a single location. This can be accomplished by contacting the cathode with the solid ionic membrane while the former is immersed in the molten electrolyte. At the point where all three elements are in contact with each other, transport requirements are effectively eliminated and no charge gradient within the metal-containing electrolyte develops. The triple point, however, is by necessity of small area and the process is not suitable to large scale processes. Therefore, for scale-up the process needs to be designed so that the cathodic reaction does not occur only at the triple point.

The actual reaction product at the anode is dependant upon the nature of the anionic species. Where the molten electrolyte is a molten metal oxide, the anionic species is oxygen ions. The oxygen ions will be transported across the ionic membrane and oxidized to molecular oxygen at the anode. If the anionic species is in the form of a sulfur anion, the ionic membrane is selected to conduct sulfide anions and the reaction product at the anode may be sulfur gas, such as $SO_2$ (g), where oxygen is also present, or S (g), where the temperature is greater than the boiling point of sulfur.

In the method described in this invention, many unique advantages exist over a conventional electrolysis process, in which both electrodes are in contact with the molten electrolyte. They are (1) the metal may be deposited on the electrode which increases the cathodic area and extends it into higher concentration areas in the melt, thereby making the process auto-catalytic, (2) electrical shorting of the anode and cathode does not occur because the ionic membrane or system of membranes physically and electronically separates the two electrode compartments, (3) no parasitic reverse reactions occur at the anode while depositing metals with variable valencies, (4) formation of products at the anode are not expected to increase cell resistance, and (5) for a molten metal oxide electrolyte, the reaction products in the process are only the metal and oxygen gas, thus making the process environmentally sound.

An apparatus as described in FIG. 1 may be used for the electrochemical reduction of metals whose cationic species have lower reduction potential than that of the cationic species in the ionic membrane and, in particular, for transition metals, main group metals, alkali metals, alkaline earth elements and rare earth elements. By way of example only, the apparatus may be used to reduce the following metals from a molten metal electrolyte: gold (Au), silver (Ag), nickel (Ni), cadmium (Cd), cobalt (Co), tungsten (W), tin (Sn), vanadium (V), zinc (Zn), chromium (Cr), copper (Cu), lead (Pb), iron (Fe), molybdenum (Mo), silicon (Si), magnesium (Mg), manganese (Mn), boron (B) and titanium (Ti). In order for the apparatus and method to be practicably applied to metal extraction in an industrial setting, the system must be capable of scale-up. By selection of the molten electrolyte so that the concentration gradient of anions at the molten electrolyte/ionic membrane interface is not rate controlling i.e., the diffusivity of the anion is greater than $10^{-5}$ cm$^2$/sec, and/or the molten electrolyte/ionic membrane interfacial area is sufficiently large such that the reduction reaction is rate limited at the cathode-molten electrolyte interface. There is no requirement for a triple point boundary mentioned earlier. By utilizing this feature, the entire cathode surface may be involved in the reduction reaction which greatly improves the efficiency of the process. By designing the cathode-molten electrolyte with large interfacial area, which surface area preferably also increases as the extracted metal is deposited on the cathode, the process can be made autocatalytic and extremely rapid. This process is kinetically (and economically) very attractive.

The production and efficiency of the cell can be improved by decreasing the distance between the cathode-electrolyte interface and the electrolyte-ionic membrane interface by increasing the concentration of the metal compound in the electrolyte, by stirring the melt or using other mass transport promoting steps, by using multiple cathodes, by chemically modifying the metal-containing electrolyte composition and/or by increasing the cathode-electrolyte surface area. For example, the slag composition may be adjusted to provide optimal electrolysis conditions or the metal electrolyte composition may be synthetically created by combining individual metal compounds. The composition of the electrolyte may be adjusted to lower the melting point of the electrolyte and/or to raise the ionic conductivity of the electrolyte. An oxide melt is more effective when its ionic conductivity is large and the metal ions and the oxide anions ($O^{2-}$) are free to move through the electrolyte. This tends to improve the power/yield ratio of the electrolysis. For this reason, basic metal oxides melts are favored over acidic oxide melts. A basic oxide melt can be created by adding oxides that serve as electron donors such as CaO, BaO, $K_2O$, $Na_2O$, etc.

Chemical stability and chemical compatibility of the molten metal electrolyte with the ionic membrane is also important. The composition of the electrolyte may be adjusted to reduce its reactivity with the ionic membrane. For instance, if CaO—$Al_2O_3$—$SiO_2$—FeO forms the molten electrolyte and yttria stabilized zirconia the ionic membrane, then the reactivity between the molten electrolyte and the ionic membrane can be decreased by decreasing the CaO content of the molten electrolyte or adding CaO to the ionic membrane.

Further, the composition of the molten electrolyte will change as the metal extraction process progresses, with the electrolyte becoming increasingly depleted in the metallic species being reduced. It may be desirable to adapt the apparatus for a continuous or batchwise introduction of the compound containing the metallic species to be reduced into the electrolyte. Additional electrolyte to be reduced may be added to ensure an electrolyte rich in the metallic species to be extracted. Transport properties of the molten electrolyte may be improved in a continuous or batch mode, for example, by metal-containing electrolyte composition adjustment, stirring or agitation of the electrolyte to reduce diffusion profiles which may form near the membrane and/or the cathode, as discussed above.

The ionic membrane is selected to electronically separate the molten electrolyte from the anode, i.e., to resist electron transfer from the metal-containing electrolyte to the anode. If substantially complete electronic separation (e.g., $\geq 90\%$) is not obtained, a leakage current, e.g., electronic transport across the ionic membrane, results which reduces the efficiency of the charge transfer reaction. The ionic membrane desirably exhibits high ionic character (with respect to the anion(s) of interest) and lower electronic character. By "high ionic character" it is meant that at least about 90% of the conductivity is due to ionic conductance. The balance is typically due to electronic conductance. The ionic membrane may be an ionically conductive solid, an ionically conductive liquid immiscible with the molten electrolyte, or a composite comprising, for example, a solid ionic membrane backed on its anodic side by an ionically conductive, substantially electronically non-conductive liquid membrane.

FIG. 1 is a schematic illustration of a cell including a solid ionic membrane. By "solid" as that term is used, it is meant solid at the elevated operating temperatures. The solid ionic membrane should be substantially non-porous, since any fluid pathways through the membrane may short-circuit the system. Stabilized zirconia is a preferred solid ionic membrane because it is sufficiently non-electronically conductive to serve as the ionic membrane in many systems and because it is chemically resistant to many molten metal oxide melts. Stabilized zirconia includes zirconia ($ZrO_2$) which has been doped with yttria, magnesia, calcia, etc. in order to stabilize the solid state structure and to increase the oxygen ion conductivity of the material. The solid ionic membrane may also include other fluorite structures such as hafnia and thoria, which are known to conduct oxygen ions and which have acceptable conductivity at operating temperatures. The solid ionic membrane may be formed into any shape. Solid ionic membranes are advantageous in that they form natural barriers. In other embodiments of the invention, the solid ionic membrane may be used as the container 12 for holding the molten electrolyte (see, FIG. 5) or it may make up a portion of the vessel, such as a wall or floor portion (see, FIG. 6).

Figure 2:
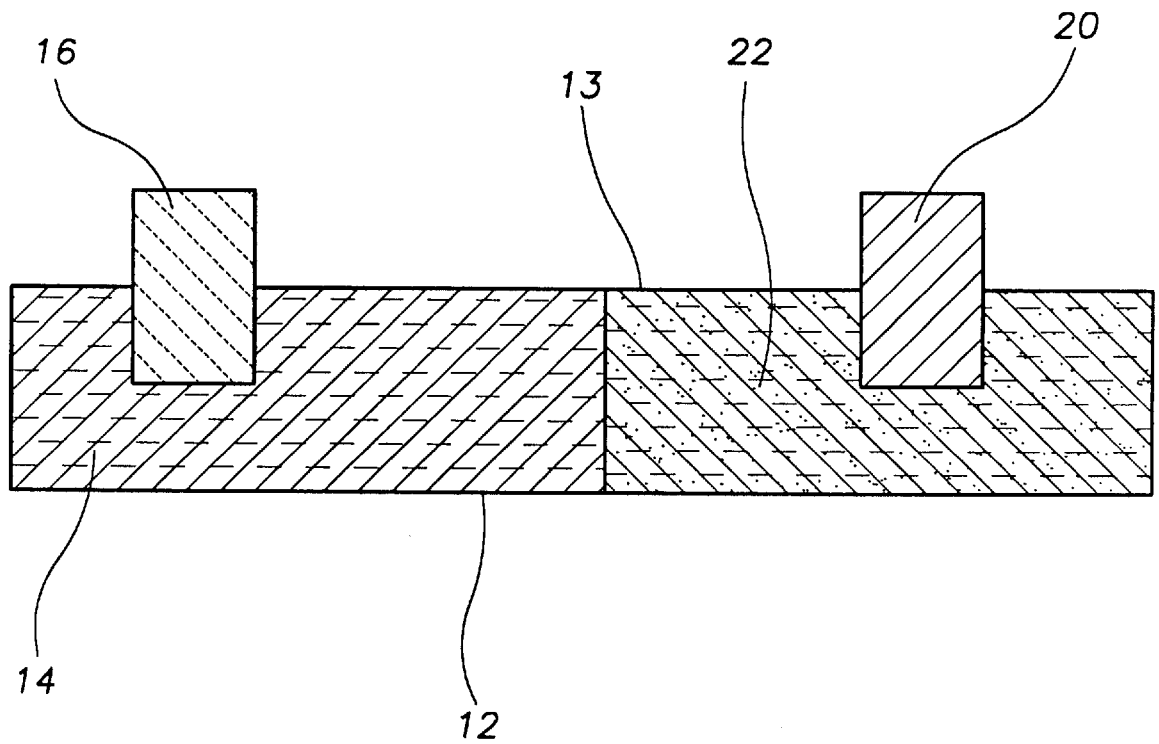
FIG. 2 is an illustration of a metal extraction apparatus of the invention containing a primary liquid ionic membrane.

FIG. 2 is a schematic illustration of a cell including a liquid ionic membrane, in which like elements are labeled as in FIG. 1. The molten metal electrolyte 14 is separated from the anode 20 by a liquid ionic membrane 22 which exhibits substantial ionic character. The liquid membrane 22 is desirably immiscible in the molten electrolyte. A suitable liquid ionic membrane includes $CaAlSiFeO_x$, where x is selected to provide a molten metal oxide with suitable oxygen ion conductivity, provided the metallic species to be reduced has a reducing potential less than that of iron. $CaAlSiFeO_x$ may be used as an ionic membrane in either a liquid or solid state, dependant upon the operating temperature. Alternatively, a semi-permeable membrane 13 may be disposed between the two to prevent undesirable mixing. Suitable semi-permeable membranes include porous and non-porous zirconia.

Figure 3:
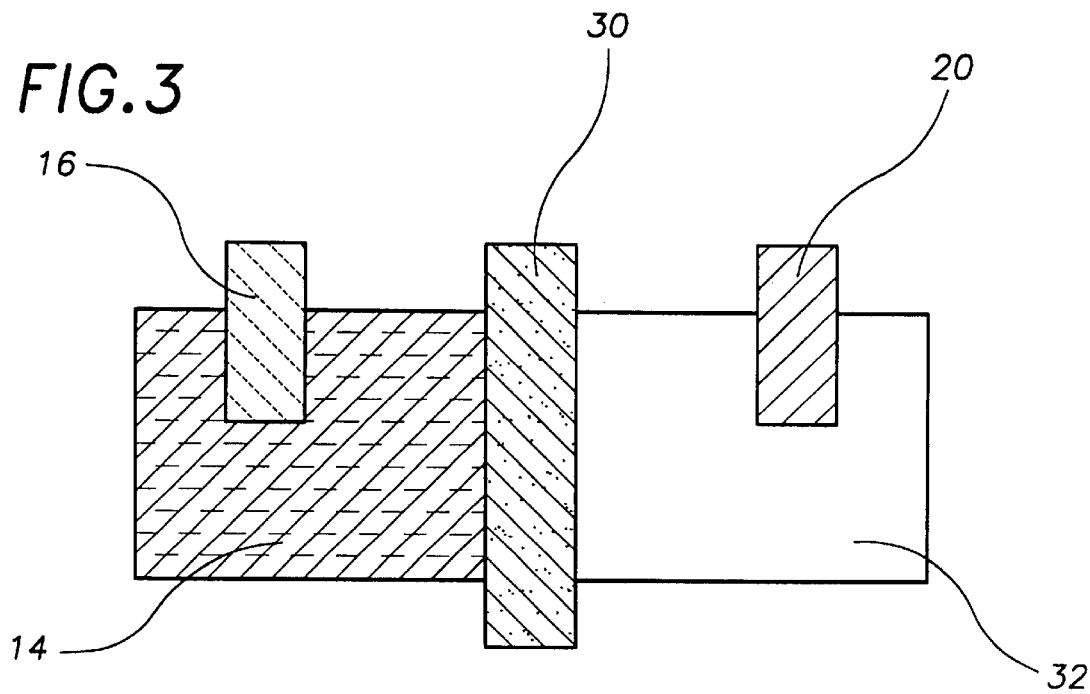
FIG. 3 is an illustration of a metal extraction apparatus of the invention containing a primary solid electrolyte-secondary liquid ionic membrane.
Figure 4:
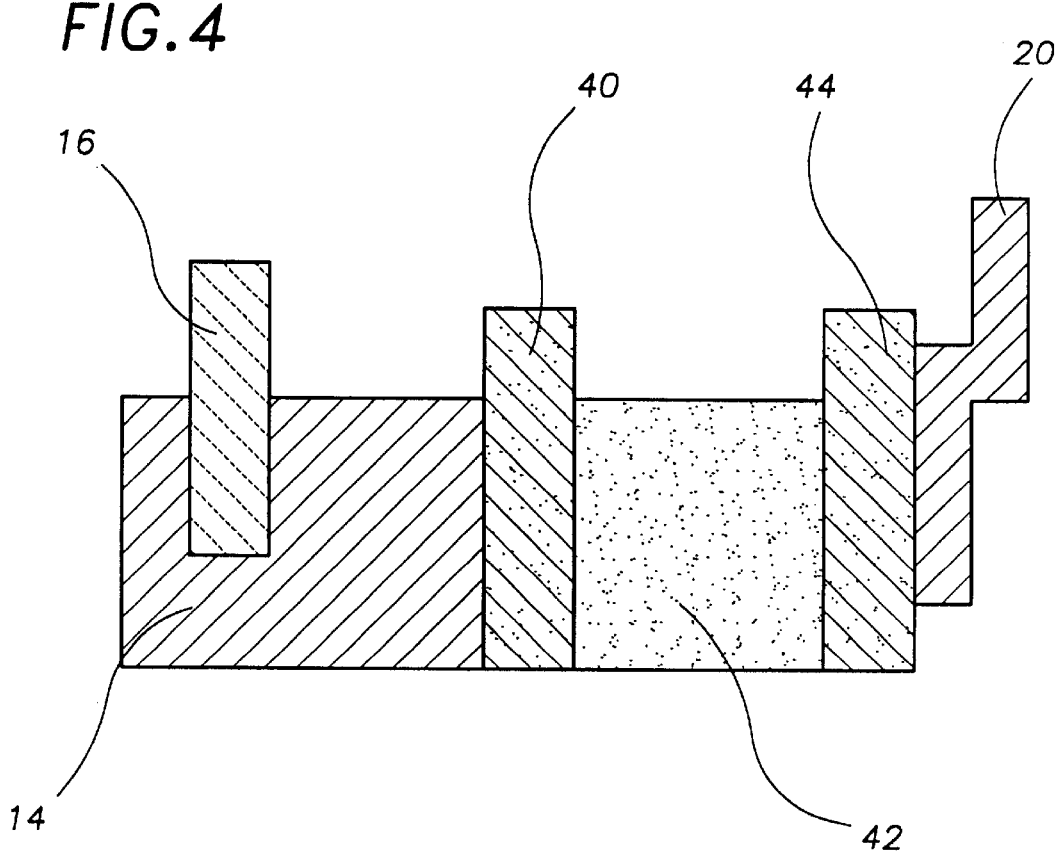
FIG. 4 is an illustration of a metal extraction apparatus of the invention containing a first solid ionic membrane, a secondary liquid ionic membrane and a second solid ionic membrane.

FIG. 3 is a schematic illustration of a metal refining apparatus possessing a primary solid ionic membrane 30 adjacent to a secondary liquid ionic membrane 32. In such a configuration, the ionic membrane 30 may have some electronic character without compromising the metals extraction process because the ionic character of the secondary membrane prevents current leakage. A suitable secondary ionic membrane includes $CaAlSiFeO_x$. FIG. 4 is an illustration of yet another embodiment of the invention, in which the metal extraction apparatus includes a first solid ionic membrane 40, a secondary liquid ionic membrane 42 and a second solid ionic membrane 44. The second solid ionic membrane 44 may be useful in the containment of the secondary liquid ionic membrane.

The amount of current to be passed through the cell will help to determine the amount of the ionic membrane surface required and will influence the location and surface area of the membrane used. Reducing the thickness of the membrane may result in lower overvoltages, however, the lifetime of the membrane may be correspondingly shortened.

Increased processing temperatures will increase the ionic conductivity of the molten electrolyte. But, at least in the case of stabilized zirconia, an increase in temperature may also increase the electronic conductivity of the ionic membrane, which will have a detrimental effect on efficiency. Deleterious effects of electronic conductivity may be reduced by using the solid ionic membrane in conjunction with secondary membranes which are strictly ionically conductive, as discussed above, thus providing a wide operating temperature range. The secondary membrane may be a second solid membrane with different electronic and ionic properties or it may be a liquid membrane.

The cathode(s) is expected to be similar to those used in normal electrolysis of the metal of interest; however, there may be special requirements due to the high temperatures and chemical corrosiveness of the electrolyte under use conditions. The cathode should not be reactive with either the product metal or with the molten metal electrolyte. In most cases, the cathode will consist of some form of the product metal, e.g, an alloy thereof, and may include the refined metal or alloy, i.e., through dendritic growth. The cathode is in electrical contact with the oxide metal melt and will increase the efficiencies of electrolysis when placed close to the ionic membrane. The cathode may be either liquid or solid and the effective surface area may change (an preferably increase) as the product metal is formed, e.g., through endritic metal formation or metal pooling at the cathode.

In industrial scale reactions, the apparatus may optionally include several athodes, which operate simultaneously and/or an individual cathode of high surface area in the form of a mesh or grating. This will increase cell current and enhance mass transfer of the system.

In another embodiment of the invention, a cathode is employed which has electrical contact, but not physical contact, with the molten electrolyte. In this embodiment, the cathode forms a plasma arc at the exposed surface of the melt in an electrochemical cell otherwise substantially similar to those described herein. The plasma arc-generating cathode provides a source of electrons and an area for cathodic charge-transfer reactions.

The anode is typically located on the opposite side of the membrane from the molten electrolyte. For those embodiments in which a solid ionic membrane is used, the anode is surrounded by a reference gas. The anode is desirably inert to the oxidation product produced at the anode, which in most cases is a gas such as oxygen or sulfur. By utilizing a slightly reducing reference gas, e.g., 1% $H_2$ in nitrogen, it may be possible to use a stable nickel or molybdenum gauze electrode or a ceramic/metal composite electrode while still maintaining the electronic integrity of the membrane. When the anode is immersed in a liquid ionic membrane, the anode is desirably inert to the liquid as well.

In other preferred embodiments, it may be desirable to use reference electrodes in the refining process. The reference electrodes may be positioned so as to give an accurate determination of the potential at the cathode. This is useful when the electrolyte contains more than one metal and one wishes to selectively extract a single metal at a time. Arrangement and use of reference electrodes is discussed in greater detail with reference to metal sensors below.

In use, a cell may be prepared as described herein and/or as shown in any of FIGS. 1 through 8 and the apparatus is charged with a metal oxide slag or other electrolyte. The slag may be a waste metal oxide slag or flux residue from conventional metals processing. The slag may be introduced into the apparatus at room temperature in a solid state and subsequently heated to form the molten metal electrolyte. In other preferred embodiments, the slag is introduced into the apparatus vessel at elevated temperatures in a solid or liquid state. The molten metal oxide slags are maintained at temperatures in the range of about 400–2000° C., and preferably about 1200–1600° C., during the refinement process. The actual operating temperature will depend in part on the electrolyte composition. For example, where it may be desired to operate at lower electrolyte temperatures, e.g., 400–900° C., beryllium oxide may be added to a metal oxide electrolyte. Beryllium oxide has been shown to improve ion mobility and ion diffusivity at lower operating temperatures. Stabilized zirconia ionic membranes may be used for refinement of metals at temperatures up to about 1500° C. and at applied potential of about 1–3 volt. At higher temperatures and/or potentials, cell modification to minimize current leakage is advantageous, e.g., use of a double ionic membrane. The electrolyte may be maintained at a desired temperature using conventional heating techniques, such as external or internal resistive heating or inductive heating.

A potential is then applied across the anode(s) and cathodes(s) which reduces a specific metallic species into the pure metal according to the half reactions as shown generally in eqs. (1) and (2). Alternatively, an alloy of two or more metals may be obtained by selecting a potential which simultaneously reduces more than one metallic species into their respective metallic states. For example, when the potential is about 1.3 V, both iron and chromium may be reduced at about 1500° C. and a chromium-iron alloy is obtained.

Figure 5:
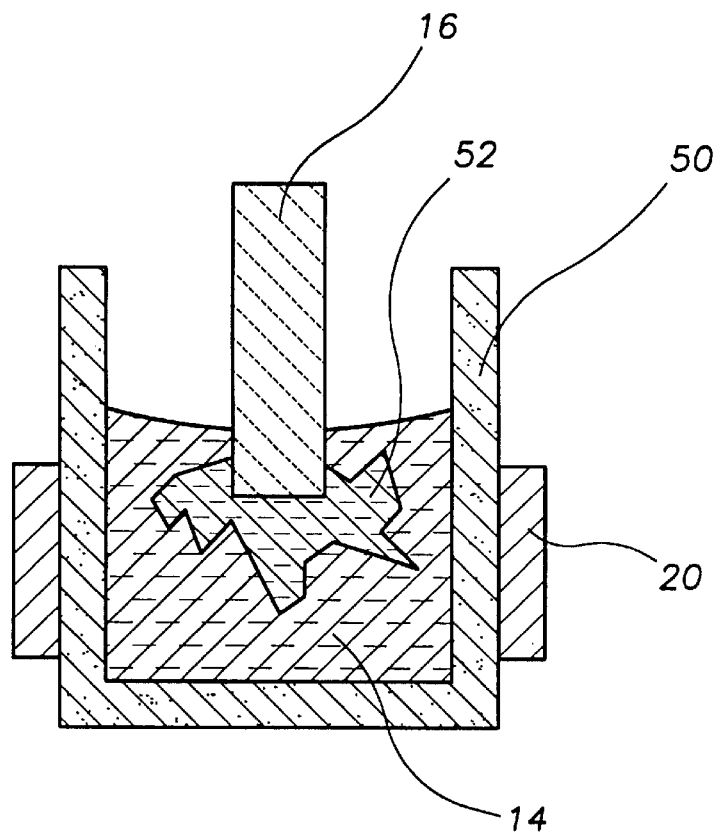
FIG. 5 is an illustration of a metals refining apparatus in which a solid ionic membrane is used as the vessel for holding the metal-containing electrolyte.
Figure 6:
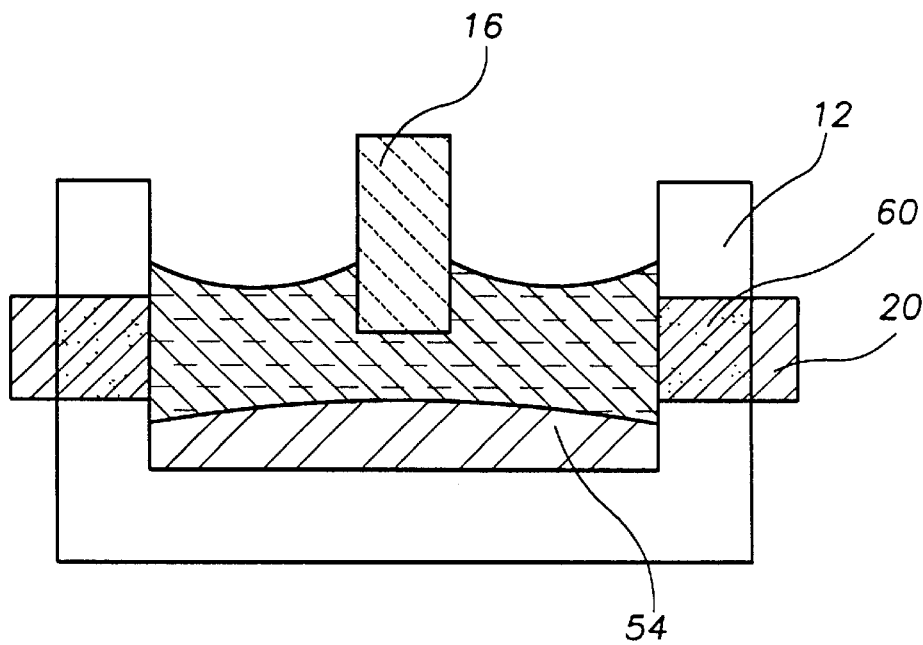
FIG. 6 is an illustration of a metals refining apparatus in which the ionic membrane comprises a portion of the vessel for holding the metal-containing electrolyte.
Figure 7:
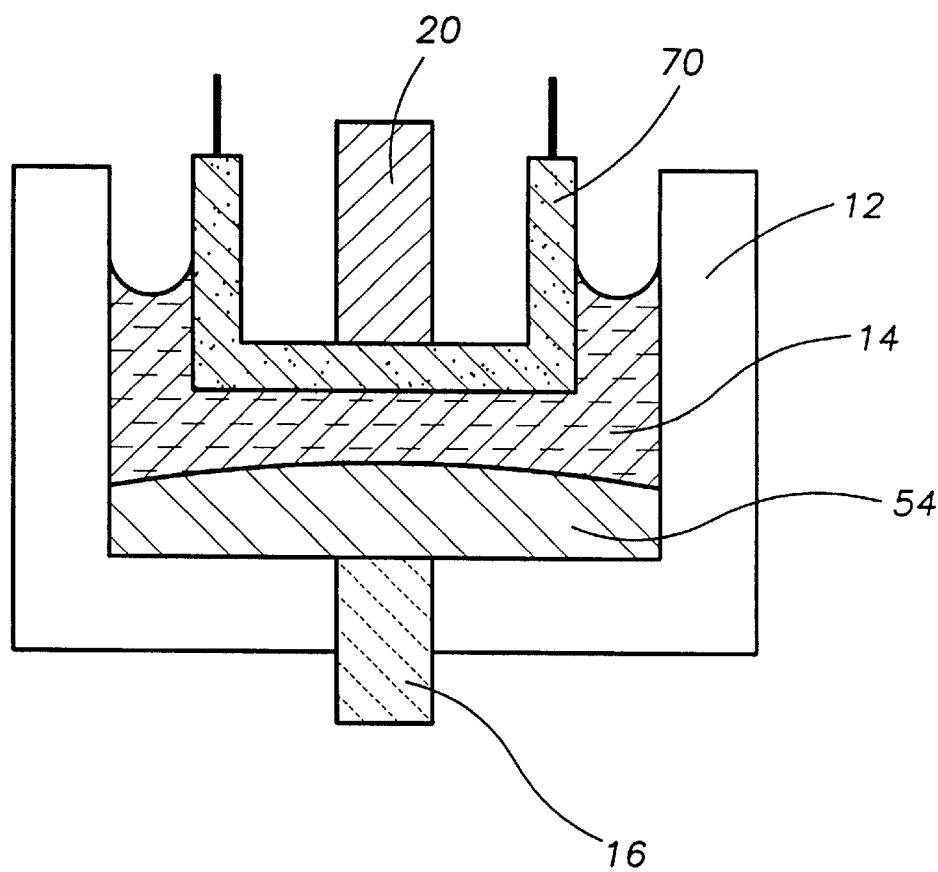
FIG. 7 is an illustration of a metals refining apparatus in which the cathode is located at the bottom of the holding vessel.
Figure 8:
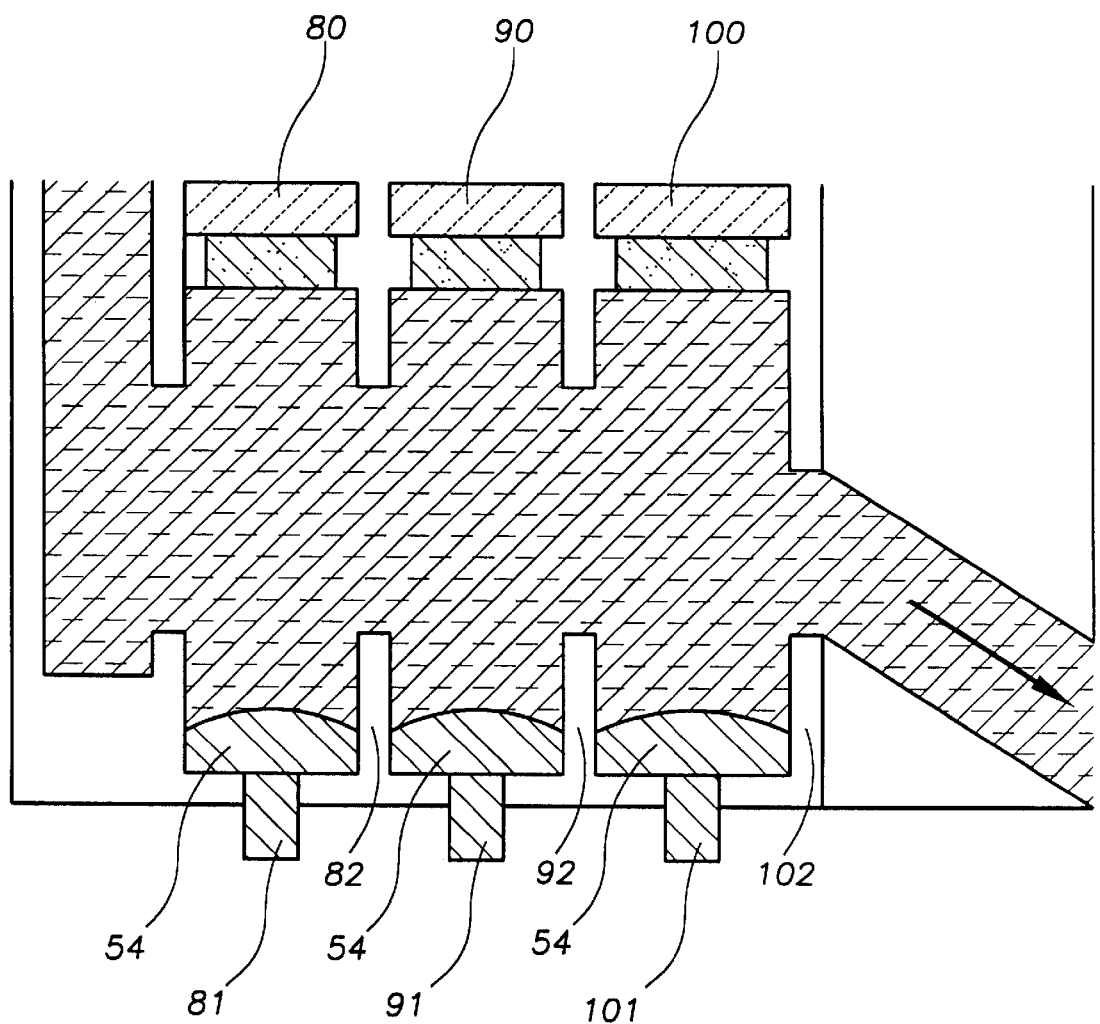
FIG. 8 is an illustration of a metals refining apparatus in which a plurality of electrolytic cells each capable of metals refining are set up in series.

The process may be carried out in either a batch process or continuous process mode. A crucible-batch process could use a solid ionic membrane 50 as the vessel holding the molten metal electrolyte, as shown in FIG. 5. FIG. 5 also illustrates the formation of product dendrites 52 at the cathode which can increase cathode surface area for charge transfer reaction and which can intrude even further into the molten metal electrolyte as the reaction progresses. The metal dendrites enter metal-rich slag and simultaneously provide a shorter path for the $O^{2-}$ ions to migrate towards the ionic membrane. This is potentially an autocatalytic process as the reaction kinetics may be enhanced by the formation of the metal dendrites. The effect of such dendrite formation is that the electrode surface area for charge transfer reaction increases and the electrolysis process does not behave as if the reaction were material transfer limited. In order to take advantage of this, the metal must exist as a solid at the temperatures of operation. Where the electrolyte is maintained at temperatures above the melting point of the product metal, a molten metal pool 54 of denser metal will form at the base of the crucible, as shown in FIGS. 6–8. Alternatively, where the metal is less dense than the molten metal electrolyte, the metal will collect on the upper surface of the electrolyte. Separation of the refined metal from the electrolyte may be accomplished by siphoning the metal from the crucible. In still another embodiment, at operating temperatures above the boiling point of the refined metal, the metal may form as a gas, e.g., zinc, magnesium, etc. In such cases, the metal may be collected and condensed in a secondary chamber.

Depending upon the quantity of current to be passed through the cell, the ionic membrane may only be required to occupy a fraction of the crucible surface. For example, some of the insulating brick lining the interior of a furnace could be replaced with ionic membrane "bricks" 60, as shown in FIG. 6. This embodiment represents an appealing low cost approach, as the ionic membrane may be less expensive as a brick than as a crucible.

In another embodiment of the invention, the cathode 16 may be located at the base of the vessel 12 and the ionic membrane may be introduced from above as a series of tubes or plates 70, as shown in FIG. 7. In this embodiment, the molten metal pool 54 serves to increase the cathode surface area.

In yet another embodiment of the present invention, several electrolytic cells may be connected in series, with each cell able to independently apply a potential to the electrolyte. An example of such an apparatus is illustrated in FIG. 8, where anode, cathode pairs 80, 81 and 90, 91 and 100, 101, respectively, are capable of independent operation.

Each of the electrode pairs is separated from its neighboring electrodes by a partial partition, 82, 92, and 102, respectively, to create a cell. This series of electrochemical cells may operate like an electrochemical sieve. The first electrode pair applies a potential selected to reduce the most easily dissociable species in the electrolyte, and each succeeding electrode pair may be responsible for reduction of the next species in the electropotential series. By control of the flux (flow of material through the vessel), furnace temperatures, and operating potentials within each cell, it may be possible to substantially completely remove the selected species before the electrolyte flows to the next cell. This process may be advantageous because the electrolyte to be refined continuously flows through the apparatus.

Further modifications to the apparatus and its method of operation are contemplated as within the scope of the invention. For example, apparatus designs may include inverted crucible arrangements and shaft processes. It is also within the scope of the invention, to operate the apparatus as a continuous process, for example, by collecting the product as a molten metal at the bottom of the vessel which is continuously removed from a tap hole located there.

The metals refining process of the invention may be practiced using metal-containing electrolytes containing anionic species in addition to or in place of oxides. For example, when the molten metal electrolyte includes metal sulfides and/or metal halides, the ionic membrane is selected for its ability to transport sulfide and/or halide anions. The use of a chlorine ion-selective membrane may be very useful in the production of aluminum; and the use of a sulfur ion-selective membrane may be very useful for metal extraction from sulfide mattes. By way of example only suitable ionic membranes for the ionic conduction of sulfides include calcium sulfate and calcium sulfate mixed with zirconia. The use of stabilized zirconia results in a more compact ionic membrane. By way of example only, suitable ionic membranes for the ionic conduction of halides, such as fluorides, includes calcium fluoride. Other alkaline earth halides are contemplated for use as an ionic membrane in accordance with the invention.

Sensor for determination of metal composition.

The present invention represents an advance over conventional aqueous solution-based electrolytic principals for the electrolysis of molten electrolytes. Quantitative measurement of the electrolytic process is accomplished by using the ionic membrane as a reference electrode base for the precise determination of the electrolyte potential and to electronically separate the anode and cathode. An in situ electrochemical technique for measuring the concentrations of easily dissociable oxides in slags at elevated temperatures is described. The technique consists of using an ionic membrane, such as stabilized-zirconia solid electrolyte by way of example, to separate a reference-gas compartment from the slag or metal-containing electrolyte of interest.

Three types of measurements may be used to obtain information concerning the slag phase composition and transport properties.

An open circuit voltage measurement (Type I) between a reference gas and the slag phase gives a resting potential of the system and which can provide information about the oxygen potential of the system. This information is currently provided by conventional oxygen sensors and may be used in conjunction with the following amperometric measurements of the invention.

In one embodiment of the invention (type II measurement), a potentiostat is used to apply a direct current-potential sweep or a potential step between the inner and outer compartments of the cell, driving oxygen ions from the slag into a reference gas. The resulting current-potential profile measured utilizing the reference electrodes reveals the dissociation potential and concentration profile of dissociable oxides. The potential indicates the type of cation present and its thermodynamic activity within the slag, while the current-time profile reveals the relative concentration and transport properties of such cations within the slag. The technique can therefore determine multiple properties of several different cations with only one measurement.

In a second embodiment of the invention (type III measurement), a potentiostat is used to carefully electrolyze a known, small volume of slag by removing large quantities of oxygen ions from the molten metal electrolyte (slag) into the reference gas. The coulombs of charge, q, at different applied potentials can be used as a direct indication of the concentration of each dissociable oxide species present within the slag.

The sensor of the invention provides the same information available with conventional potentiometric sensors (when potential is measured in an open circuit) while concurrently providing data concerning the concentration of the metal species and the diffusion kinetics of the species within the molten metal electrolyte.

A type I open-circuit potential (OCV)/oxygen-activity measurement device is represented by the electrochemical cell: cathode (working electrode)/electrolyte/ionic membrane/anode (counter electrode)/air.

The operation of the apparatus of the invention will be described with reference to an oxide slag as the electrolyte and partially-stabilized zirconia (PSZ) as the solid ionic membrane. This is for the purposes of discussion and illustration only and the principles of the invention may be applied to a large number of electrolytes and ionic membrane systems.

A reference oxygen compartment is separated from the oxide slag using a solid electrolyte ionic membrane, here PSZ. The reference partial pressure of oxygen can be either set up by a metal/metal oxide mixture or by a gas phase of known oxygen activity.

One electrode is placed in contact with the PSZ membrane in the reference gas compartment and the other electrode is placed in contact with the slag phase.

The oxygen activity of the slag, which should be uniform in the bulk, can be determined from the open circuit potential using the Nernst equation:

$$E_{Nernst} = \frac{RT}{4F} \ln\left(\frac{a_{O_2}^{slag}}{P_{O_2}^{gas}}\right)$$

The oxygen activity within the slag may be correlated to the relative activities of transition metal oxides such as those of iron, FeO and $Fe_2O_3$, via the following equilibrium reaction:

$$4FeO + O_2 = 2Fe_2O_3$$

The Nernst equation can then be modified as follows:

$$E_{Nernst} = \frac{RT}{4F} \ln\left(\frac{1}{P_{O_2}^{gas}}\left(\frac{(a_{Fe_2O_3}^{slag})^2}{(a_{FeO}^{slag})^4}\right)\right) + \frac{\Delta G^\circ}{4F}$$

where $\Delta G^\circ$ is the standard free energy of reaction of the above equilibrium reaction.

If the slag electrode or the cathode is made of pure iron, then for small oxygen activities within the slag, the equilibrium reaction would be:

2Fe+O$_2$=2FeO

If this is the case, then the Nernst equation may be written as:

$$E_{nernst} = \frac{RT}{4F} \ln\left(\frac{1}{P_{O_2}^{gas}} \left(\frac{a_{FeO}^{slag}}{a_{Fe}}\right)^2\right) + \frac{\Delta G°}{4F}$$

Some FeO activity sensors make use of the above relationship. This is a simple measurement which yields thermodynamic information concerning the oxidation state of the slag and under proper conditions, can yield activities or ratios of activities when transition metal species are present as oxides in the slag. Here transition metal species implies metal species having variable valencies.

Further valuable information regarding the composition of the slag is obtained by using a type II or type III amperometric measurement. A type II measurement allows the local thermodynamic state of the slag in contact with the working electrode, WE2, to be perturbed in order to measure the response of the system. By varying the potential applied to WE2 and measuring it using the second reference electrode, RE2, information concerning the type, concentration, diffusion coefficient, and bulk transport number of dissociable oxides within the slag can be obtained.

Figure 9:
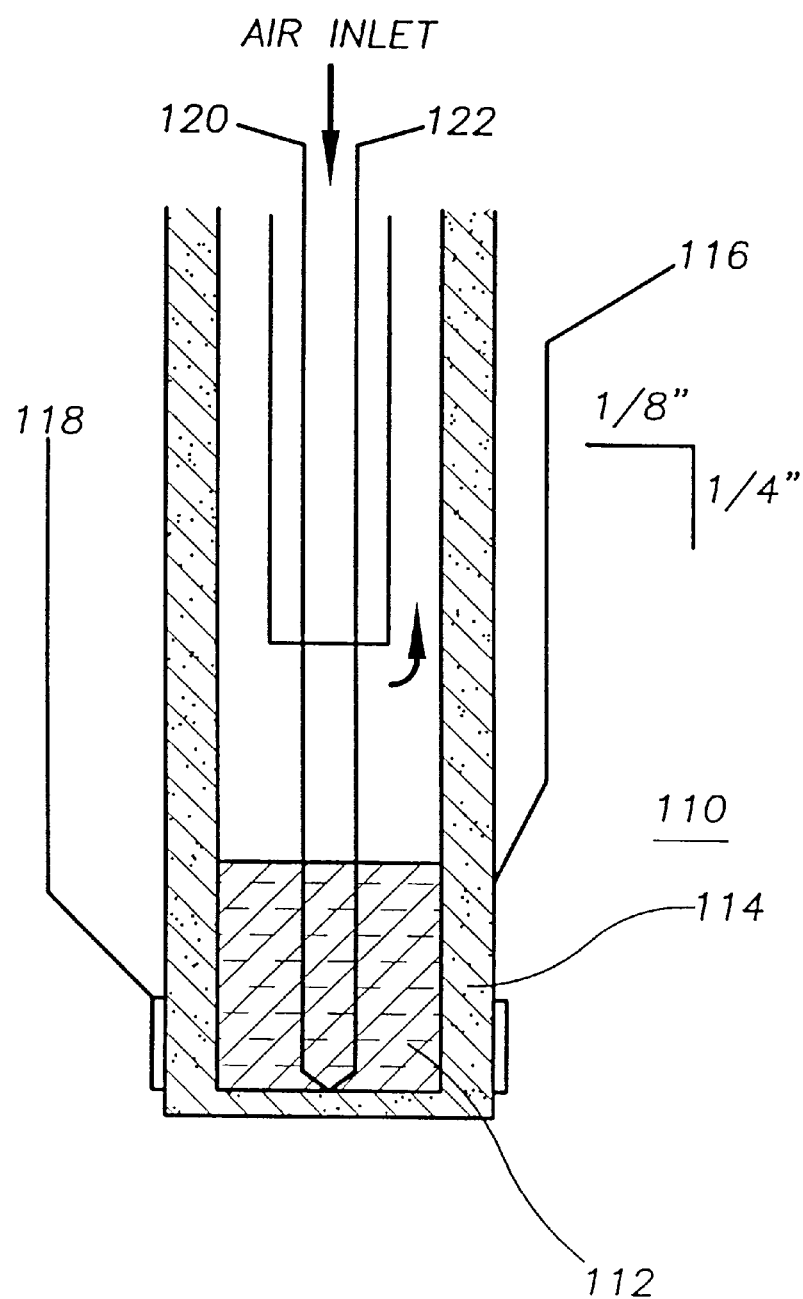
FIG. 9 is a schematic illustration of a Type II metal sensor apparatus of the invention.

A type II amperometric measurement device is shown in FIG. 9. A reference oxygen compartment 110 is separated from a molten oxide slag phase 112 using an ionic membrane 114, e.g., partially-stabilized zirconia (PSZ), as the sensor apparatus vessel. The reference compartment should contain air in order to avoid alteration of the partial pressure of oxygen as current is passed through the cell. Two electrodes 116, 118 are located in the reference gas chamber. A reference electrode 116 (RE1) is physically separated from the anode 118, or counter electrode, and is used to accurately control the applied potential on the cathode, or working electrode. The cathode 120, or working electrode, and a second reference electrode 122 (RE2) of known surface area are welded together and positioned in the slag such that the diffusion profiles can be easily modeled. RE2 is used to eliminate iR potential drops along the working electrode. For best operation, the electrode area of the combined cathode 120 and RE2 122 should be considerably smaller than that of the anode 118. Using a potentiostat, the potential of RE2 and the cathode can be accurately set to any potential relative to RE1 by passing current between the cathode and anode. This iR-compensation-current-interruption technique can detect and eliminate the additional iR drop occurring within the slag or ionic membrane to provide greater accuracy of the half-cell potential of RE2.

The thermodynamic principles upon which the measurement is based is described. The Nernst equilibrium reactions and equations set forth above in OCV measurements are also valid for Type II measurements because the oxygen partial pressure at RE2 is determined by an OCV measurement relative to the RE1 which remains unpolarized. The activity of dissociable oxide species at the slag/electrode interface can be set externally using a potentiostat.

For a slag containing only iron oxide as an easily dissociable species, the ollowing reactions will occur, depending upon the applied potential:

| Cathode | RE2 and working electrode/slag interface |
|---|---|
| $2Fe^{3+} + 2e^- = 2Fe^{2+}$ | for potentials more negative than dissociation potential of $Fe_2O_3$ |
| $Fe^{2+} + 2e^- = Fe$ | for potentials more negative than dissociation potential of FeO |
| Anode | Re1 PSZ/counter electrode/gas interface |
| $O^{2-}{}_{PSZ} = 1/2\ O_2 + 2e^-$ $Fe_2O_3$ | for potentials more negative than dissociation potential of $Fe_2O_3$ |
| Junction | PSZ/slag interface |
| $O^{2-}{}_{slag} = O^{2-}{}_{PSZ}$ $Fe_2O_3$ | for potentials more negative than dissociation potential of |

The application of a potential sweep or step to RE2 v. RE1 near the dissociation potential of an oxide will cause a significant concentration gradient to develop between the electrode/slag interface and the slag bulk. The current passing through the working electrode and counter electrode is directly proportional to the flux of the dissociating species to the electrode/slag interface. The resulting diffusion profiles generated near the electrode surface can be described by Fick's first law for systems containing a boundary layer or by Fick's second law for stagnant slag systems.

For systems containing a well-defined boundary layer, the current would be dependent upon both the bulk and electrode surface concentrations of $Fe^{3+}$ and $Fe^{2+}$. Assuming that the diffusion of a newly created $Fe^{2+}$ away from the electrode does not become rate limiting, then when potentials more negative than the ferric oxide dissociation potential but less negative than the ferrous oxide dissociation potential are applied, the following equation holds:

$$i = nFAJ_{Fe^{3+}} = nFAD_{Fe^{3+}} \frac{(C_{Fe^{3+}}^{bulk} - C_{Fe^{3+}}^{electrode})}{x}$$

where i=current; n=charge-transfer number; A=effective surface area of the electrode; j$_j$=flux of species j across the boundary layer; D$_j$=steady state diffusion coefficient of j; C$_j$=concentration of species j and x=distance across the boundary layer.

When a more negative potential than the dissociation potential of FeO is applied, increased currents associated with the additional reduction of $Fe^{2+}$ to Fe would be measured. The additional flux associated with the reduction of $Fe^{2+}$ may be approximated by the equation:

$$i = nFAJ_{Fe^{2+}} = nFAD_{Fe^{2+}} \frac{(C_{Fe^{2+}}^{bulk} - C_{Fe^{2+}}^{electrode})}{x}$$

If dendrites of electrolytic iron are formed, the effective electrode area will not remain constant, leading to further increase in resulting current.

The magnitude of the current under stagnant slag conditions can be described by Fick's second law and is dependent upon both the bulk and electrode surface concentrations of $Fe^{3+}$ and $Fe^{2+}$. When potentials more negative than the ferric oxide dissociation potential but less negative than the ferrous oxide dissociation potential are applied, the following equations hold, where t=time:

$$i(t) = \frac{3FAD_{Fe^{3+}}^{1/2} C_{Fe^{3+}}^{bulk}}{\pi^{1/2} t^{1/2}(1+\xi\theta)}$$

$$\xi = \left(\frac{D_{Fe^{3+}}}{D_{Fe^{2+}}}\right)^{1/2}$$

$$\theta = \frac{C_{Fe^{3+}}^{electrode,t}}{C_{Fe^{2+}}^{electrode,t}}$$

When a more negative potential than the dissociation potential of FeO is applied, increased currents associated with the additional reduction of $Fe^{2+}$ are measured. The additional flux associated with the reduction of $Fe^{2+}$ for stagnant slag may be approximated by the equation:

$$i(t) = \frac{3FAD_{Fe^{3+}}^{1/2} C_{Fe^{3+}}^{bulk}}{\pi^{1/2} t^{1/2}} + \frac{2FAD_{Fe^{2+}}^{1/2} C_{Fe^{2+}}^{bulk}}{\pi^{1/2} t^{1/2}}$$

By comparing the applied potential with the dissociation potentials for easily dissociable oxides, the resulting currents can be assigned to the appropriate oxide species. Strictly speaking, the above equations are only valid for small concentrations of dissociable oxides. As the concentration of dissociable oxide increases, the diffusion coefficient may become a function of the local concentration of the species being removed, tending to complicate the situation as the relationship between diffusion coefficient and concentration is ill-defined. The analysis reasonably assumes a constant diffusion coefficient. The flux equations should further be modified to account for the presence of a number of dissociable oxide cations in the bulk of the slag. Iron and steelmaking slags typically contain free cation species, such as $Mg^{2+}$, $Ca^{2+}$, $Fe^{3+}$ and $Fe^{2+}$. Si- and Al-containing species need not be considered because these cations are found with large anions, resulting in low mobility. Conductivity data for various iron oxide-containing slags are known. See, Q. Jaio and N. Themelis *Metallur. Trans.* B 19B:133 (Feb, 1988). For slags containing multiple mobile cationic species, the flux equations may be modified by a constant factor:

$$i_{tot,j} = \frac{i_{diff,j}}{K}$$

$$K = 1 - \frac{t_j^n}{z_j}$$

where $t_j$=transport number of species j within the bulk; and $z_j$=charge of species j, so that the current-defining equation involving $Fe_2O_3$ and FeO becomes, $$i_{tot}(t) = \frac{3FAD_{Fe^{3+}}^{1/2} C_{Fe^{3+}}^{bulk}}{\pi^{1/2} t^{1/2}(1 - t_{Fe^{3+}})} + \frac{2FAD_{Fe^{2+}}^{1/2} C_{Fe^{2+}}^{bulk}}{\pi^{1/2} t^{1/2}(1 - t_{Fe^{2+}})}$$

The above equations have described a response expected as a result of a constant applied potential. Comparison of responses obtained experimentally against these equations will provide information regarding the type of and amount of metallic species present in the system along with their transport properties.

An alternative technique is to apply a sweep potential. This would allow a broad range of potentials to be investigated with only one measurement. The resulting current-potential profile would exhibit a current peak near each potential corresponding to the dissociation of oxides within the slag and its concentration in the slag. A thorough mathematical treatment describing the formation of these peaks in aqueous chemistry conditions is covered Bard and Faulkner (*Electrochem. Methods* Chapter 6, John Wiley and Sons, 1980), which may be applied to the molten slag systems described herein.

Figure 10:
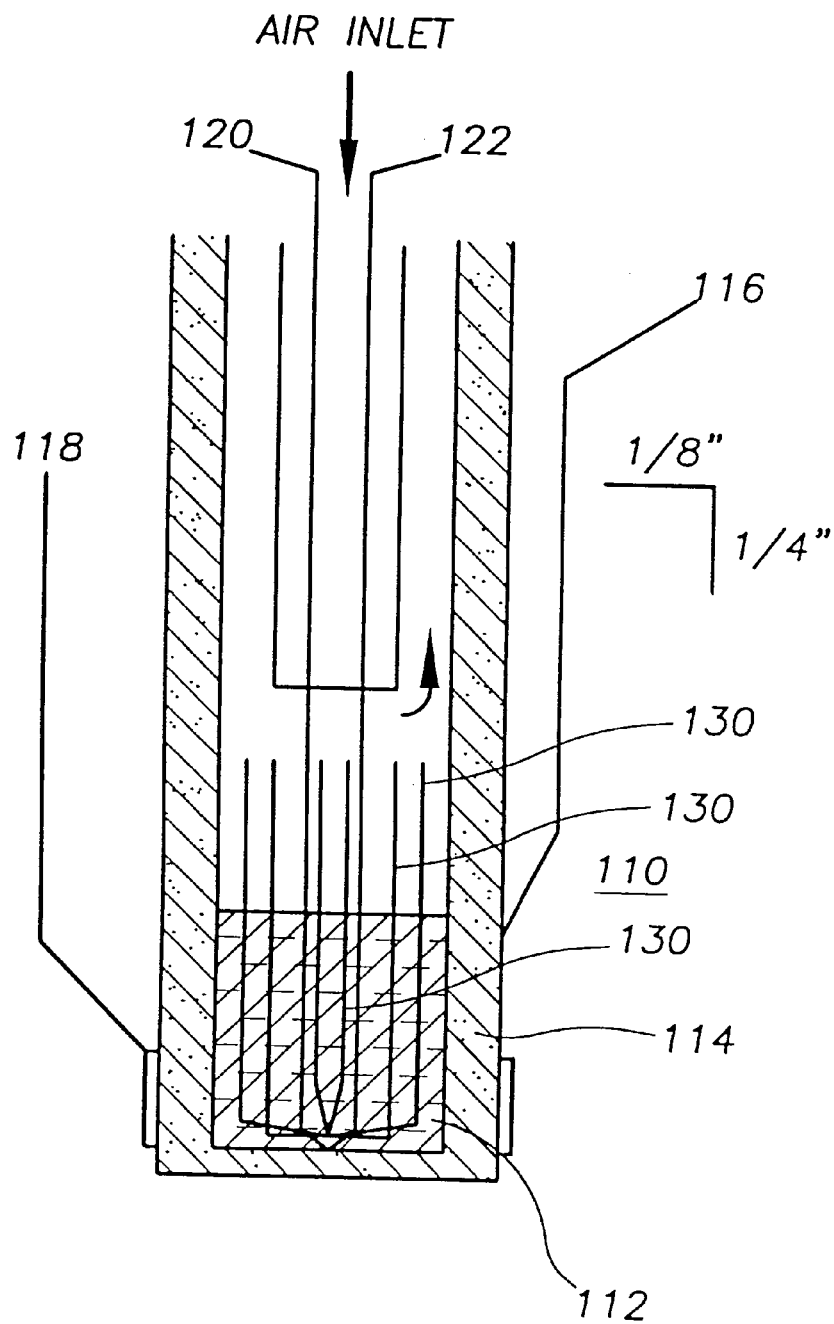
FIG. 10 is a schematic illustration of a Type III metal sensor apparatus of the invention.

A type III metal sensor apparatus is shown in FIG. 10, where like elements are similarly labeled. The apparatus is similar to that of the type II device, except that it is adapted to isolate a small known volume of slag from the slag bulk, which is then electrolyzed using a technique analogous to polarographic stripping.

A small known volume of slag may be isolated by insertion of a small crucible 130 inside the slag-containing vessel, positioned so that the isolated slag is in close proximity to the working electrode. The working electrode surface area is desirably large enough such that no portion of the enclosed slag volume is far from the electrode. This may be accomplished, for example, by using a plurality of working electrodes, or by using a gauze or foil electrode with a large surface area. A potential is then applied to RE2 which reduces only the most easily dissociable oxide species within the slag. The current at this potential is then attributed only to that species and the following electrolysis equation applies:

$$C_j = \frac{100 Q_j (MW_j)}{n_j F V_p}$$

where, $C_j$=initial wt % dissociable oxide j; $Q_j$=charge removed during electrolysis attributable to species j; $MW_j$= molecular weight of dissociable oxide j; V=volume of initial slag and $\rho$=density of the initial slag.

The application of a type III measurement at several carefully chosen potentials will yield the concentration of the dissociable oxides within the slag. The accuracy of the technique will improve with higher initial concentrations, larger transport numbers of the dissociable cation, high diffusion coefficients, longer measurement times and larger ratios of working electrode surface area to slag volume.

It is readily apparent that the sensor of the invention may be used in conjunction with the metal refining apparatus and method in order to improve the metal extraction process. Thus, the sensor method and apparatus may be used as described herein above to determine the metal electrolyte composition and the transport properties of ions in the electrolyte. This information may be used to adjust the electrolyte composition so as to improve the efficiency of the metal extraction process.

The invention is described with reference in the following examples, which are presented for the purpose of illustration only and which are in no way intended to be limiting of the invention, the true nature and scope of the invention being set forth in the claims which follow.

EXAMPLE 1

This example demonstrates the extraction of iron from a calcium silicate melt (slag).

The $CaO$—$SiO_2$—$Al_2O_3$—$Fe_2O_3$ slag system has been extensively studied and hence important parameters such as conductivity, viscosity, and phase diagrams are well known. The composition of these melts can be chosen so that they are relatively non-corrosive with respect to the PSZ. The $Fe_2O_3$ concentration was varied between 20 and 40 wt % (calculated in the system $CaO$—$SiO_2$—$Fe_2O_3$) at 5 wt % intervals.

The synthetic slags were prepared by milling $CaCO_3$, $SiO_2$, $Fe_2O_3$ and $Al_2O_3$ powders (Alfa-Aesar) in the appropriate proportions with isopropyl alcohol for 24 hours. The powder mixtures were calcined at 1000° C. for 12 hours and pressed into pellets. The pellets were placed into $Al_2O_3$ crucibles and melted in air at 1500° C. for 1.5 hours. The resulting slags were then pulverized and remelted in the PSZ sensor during the experiment. A similar process was used for preparing a slag in the system $CaO$—$SiO_2$—$Al_2O_3$—$FeO$; instead of $Fe_2O_3$, FeO was used, and the preliminary melting was done under argon at 1500° C. for 1.5 hours.

The melt containing the oxide slag was contained in a yttria-stabilized zirconia (YSZ) crucible, an ionic membrane that conducts oxygen ions. Table 1 describes the five different types of experiments conducted.

TABLE 1

Description of experiments conducted.

| name | quantity of slag | cathode surface area | PSZ surface area | cathode near PSZ | current realize |
|---|---|---|---|---|---|
| A | 1.5 g | X (wire)[1] | $Y^2$ | tip | $Z^3$ |
| B | 1 g | 2/3 X (wire) | 2/3 Y | tip | 2/3 Z |
| C | 1.5 g | ca. 2/3 X (wire) | Y | no | 2/3 Z |
| D | 1.5 g | >>X (gauze) | Y | yes | ca. 3 Z |
| E | 1.5 g | >3/2 X (wire) | Y | yes | ca. 3 Z |

[1]"X" is a given surface area; subsequent surface areas are defined as a function of X.
[2]"Y" is a given surface area; subsequent surface areas are defined as a function of Y.
[3]"Z" is a given current; subsequent currents are defined as a function of Z.

Figure 11:
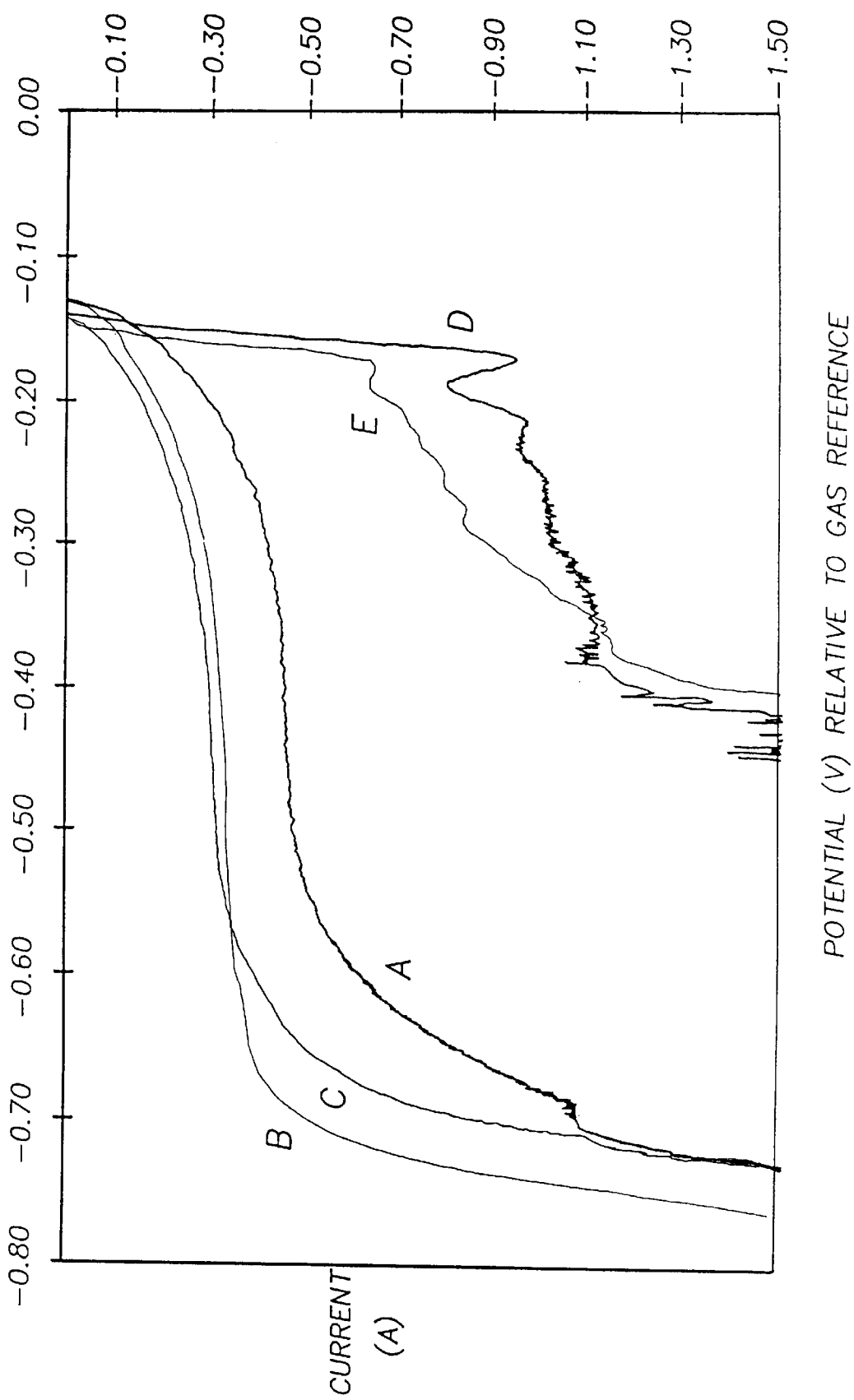
FIG. 11 is a plot of the i-V response for extraction of iron from slag from examples A through E.
Figure 12:
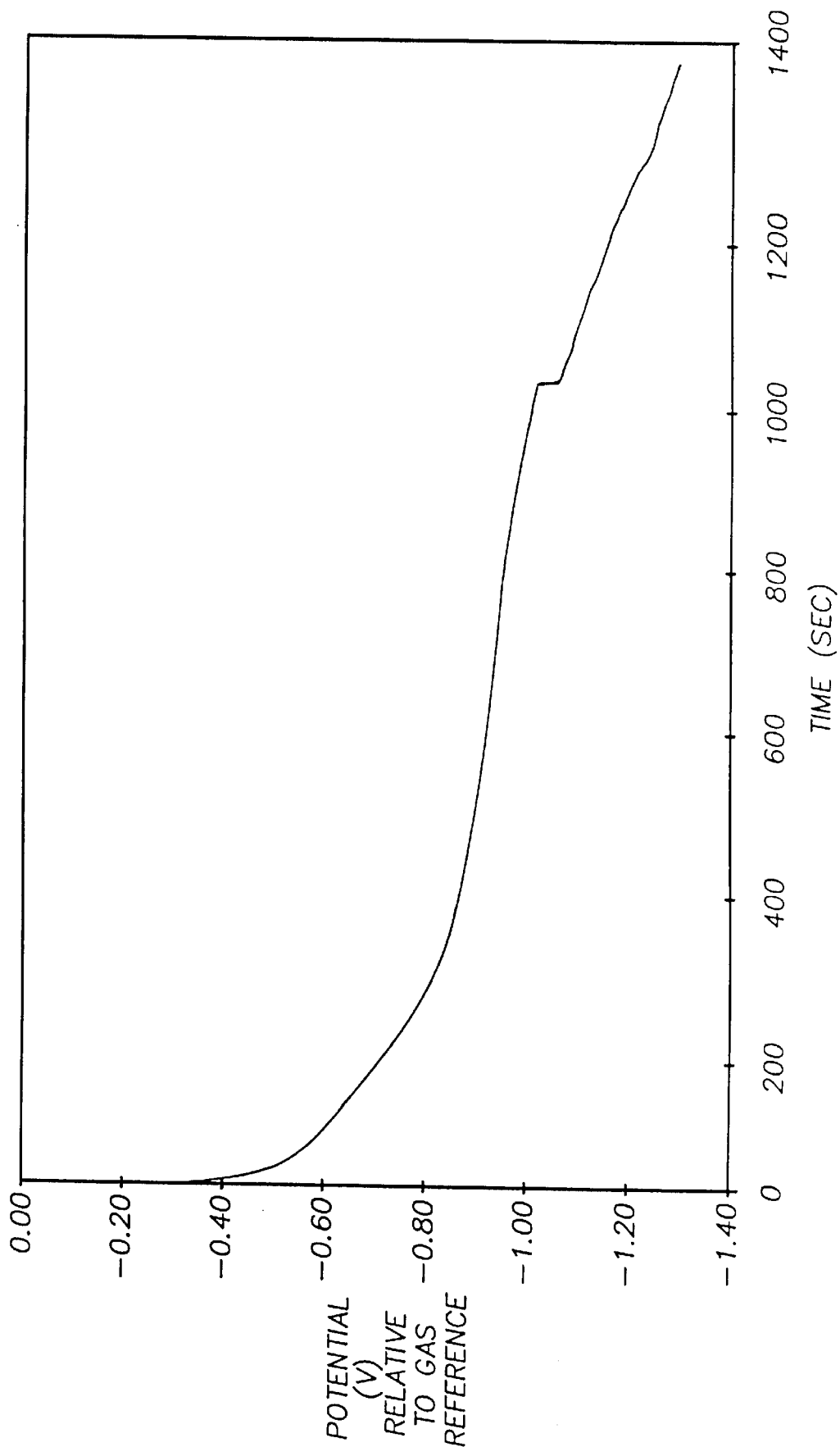
FIG. 12 is a potential-time plot for sample E of FIG. 11 at constant current of 1 amp.

Using a potentiostat, a direct current potential sweep was applied between the inner and outer compartments of the YSZ crucible, driving oxygen ions from the slag, through the YSZ crucible and into a reference gas. With the use of open-circuit-reference electrodes, the resulting current-potential profile of the experiments (FIG. 11) reveals the dissociation potential of the ferric and the ferrous oxides in the melt. The current at low applied potentials reflects the dissociation of the ferric oxide to ferrous oxide and the abrupt increase at higher potentials was caused by the autocatalytic dissociation of ferrous oxide to form iron dendrites. The post-experimental cross-section of the crucibles revealed that iron forms at the electrode-slag interface (cathode location) that is closest to the YSZ-electrode-reference gas interface (anode). Furthermore, the iron that forms at the slag-electrode interface is dendritic in nature and extends into the slag, counteracting the mass transfer limitations at the slag-electrode interface. The iron oxide in the slag can be substantially reduced prior to quenching by drawing a reduction current of 1 ampere for approximately 10 minutes. The voltage-time plot of sample E is shown in FIG. 12. From FIG. 12, the power requirement was computed to be around 1.4 KWH/kg of iron at observed current densities of around 1.8 ampere/cm$^2$-$ZrO_2$.

EXAMPLE 2

This example presents the analysis of slags with various iron oxide concentrations using Type I and II measurements. The electrochemical slag sensor of the invention may be described by the following cell:

cathode/molten metal electrolyte/PSZ/anode/air

The experimental cell as shown in FIG. 9 was used. A closed-end tube of oxygen-ion-conducting PSZ was used to separate the slag phase of interest from an external reference gas phase (air). The solid electrolyte used in the sensor was a PSZ (type ZDY-4 rom Coors Structural Ceramics), containing 9 wt % $Y_2O_3$. The compartment in direct contact with the slag was continuously flushed with argon (Grade 5 BOC Gases) at a flow rate of 14 ml/min in order to provide an inert environment. The electrode leads were positioned as follows: a dual lead counter electrode (CE), or anode, which also functioned as an S-type Pt/Pt-Rh thermocouple was attached to a Pt gauze which was sintered to the PSZ using platinum ink (Engelhard ink 9626). A reference electrode (RE1) was attached independently ¼" (0.625 cm) above the CE on the reference gas side of the PSZ using platinum ink. The platinum ink contacts were sintered during the heating up of the cell. The working electrode (WE), or cathode, and secondary reference electrode (RE2), made from Pt wire were welded together. During the measurement, the WE and RE2 are positioned in the slag such that the weld bead touches the inner bottom surface of the PSZ tube. It is not necessary for the weld bead to touch the PSZ bottom surface. The surface of the WE and RE2 which is exposed to the slag was controlled by shielding the electrodes using an alumina tube, which allowed ¼ inch (0.625 cm) of each electrode to remain unshielded. The unshielded area was kept constant in all experiments.

Figure 13:
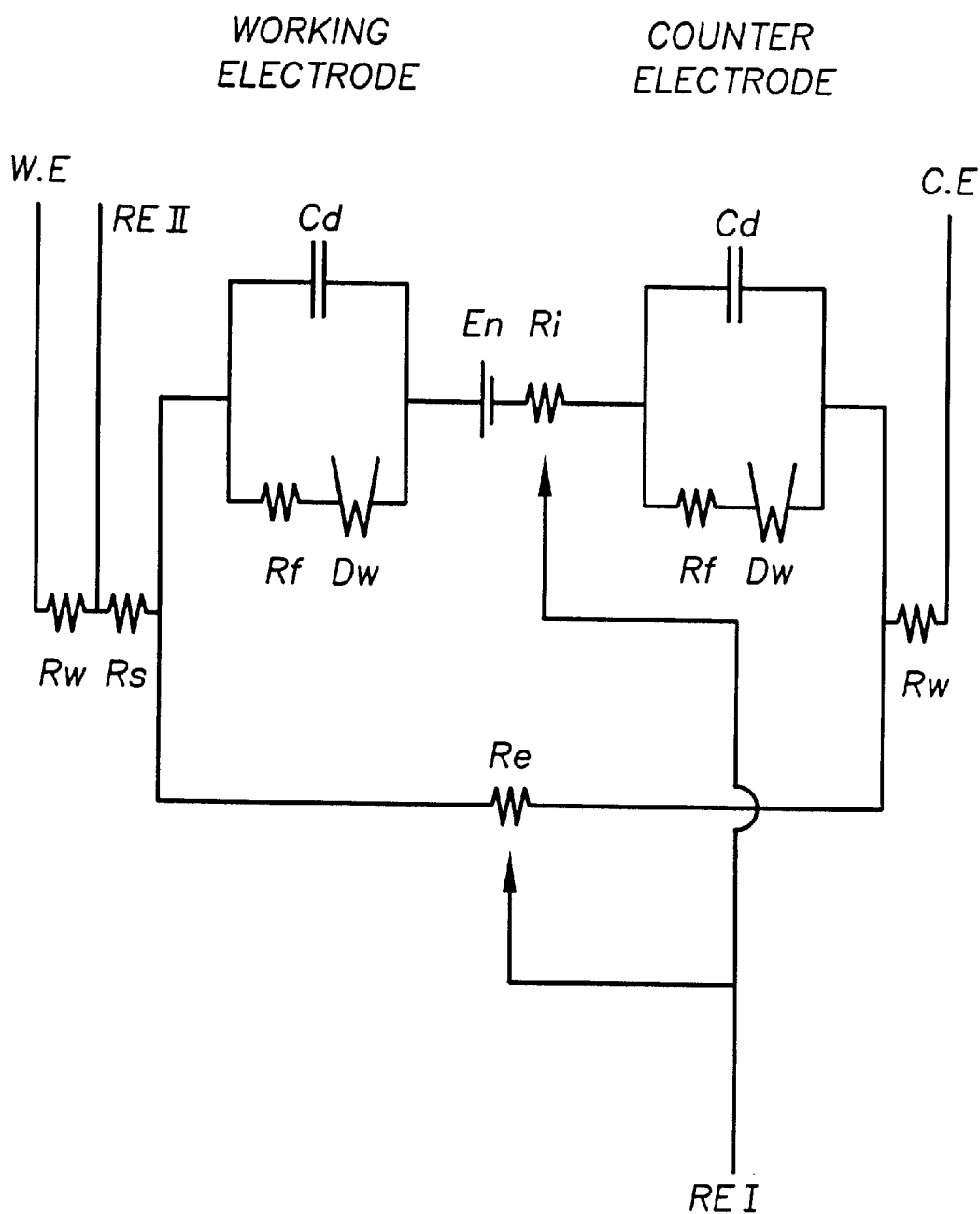
FIG. 13 is an equivalent circuit which describes the cell of FIG. 9.

The four electrode cell described above was connected to a Solartron 1287 potentiostat which controlled the potential between Re1 and RE2 by passing the required current through WE and CE. An equivalent circuit which may describe the cell is shown in FIG. 13.

The $CaO$—$SiO_2$—$Al_2O_3$—$Fe_2O_3$ slag system has been extensively studied and hence important parameters such as conductivity, viscosity, and phase diagrams are well known. The $CaO$—$SiO_2$—$Fe_2O_3$ synthetic slags used were saturated with alumina in order to stabilize the geometry of the slag sensor by preventing the dissolution of the alumina protection tube during the experiment. These melts are relatively non-corrosive with respect to the PSZ. Cell designs may eliminate the need for such precautions. The $SiO_2$/$CaO$ ratio was held constant at 1.5 for all slag compositions. The $Fe_2O_3$ concentration was varied between 20 and 40 wt % (calculated in the system $CaO$—$SiO_2$—$Fe_2O_3$) at 5 wt % intervals.

The synthetic slags were prepared by milling $CaCO_3$, $SiO_2$, $Fe_2O_3$ and $Al_2O_3$ powders (Alfa-Aesar) in the appropriate proportions with isopropyl alcohol for 24 hours. The powder mixtures were calcined at 1000° C. for 12 hours and pressed into pellets. The pellets were placed into $Al_2O_3$ crucibles and melted in air at 1500° C. for 1.5 hours. The resulting slags were then pulverized and remelted in the PSZ sensor during the experiment. A similar process was used for preparing a slag in the system $CaO$—$SiO_2$—$Al_2O_3$—$FeO$; instead of $Fe_2O_3$ FeO was used, and the preliminary melting was done under argon at 1500° C. for 1.5 hours.

The experimental i-V curves (FIG. 14) show the expected dependence of current on the initial concentration of $Fe_2O_3$ within the slag. For all concentrations of $Fe_2O_3$ tested with the amperometric sensor of the invention, the initial OCV values were identical; hence, a typical OCV oxygen sensor would not be able to directly determine a difference between these quite different slags. The plateau on the i-V curves represents the reaction $Fe^{3+}$to $Fe^{2+}$while the edge represents mainly the reduction of $Fe^{2+}$to Fe. The i-V plots shown in FIG. 14 include an uncompensated solution resistance term in the measurement which tends to shift the i-V curves towards more negative potentials, thereby distorting the i-V curve. This explains why the relative position of the edge appears to be located at more negative potentials than would be expected for FeO dissociation.

Figure 14:
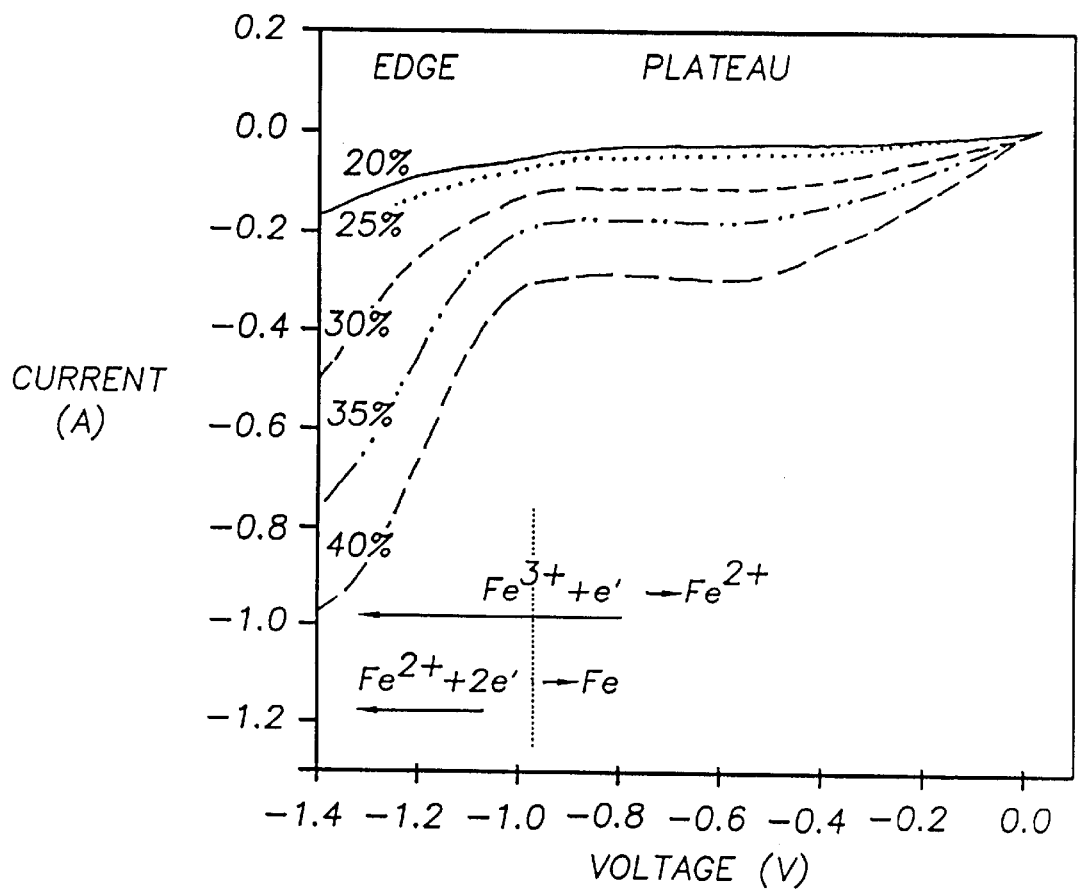
FIG. 14 is an I-V plot at 5 mV/sec for $Fe_2O_3$-containing slags where the amount of $Fe_2O_3$ varied between 20–40 wt %.
Figure 15:
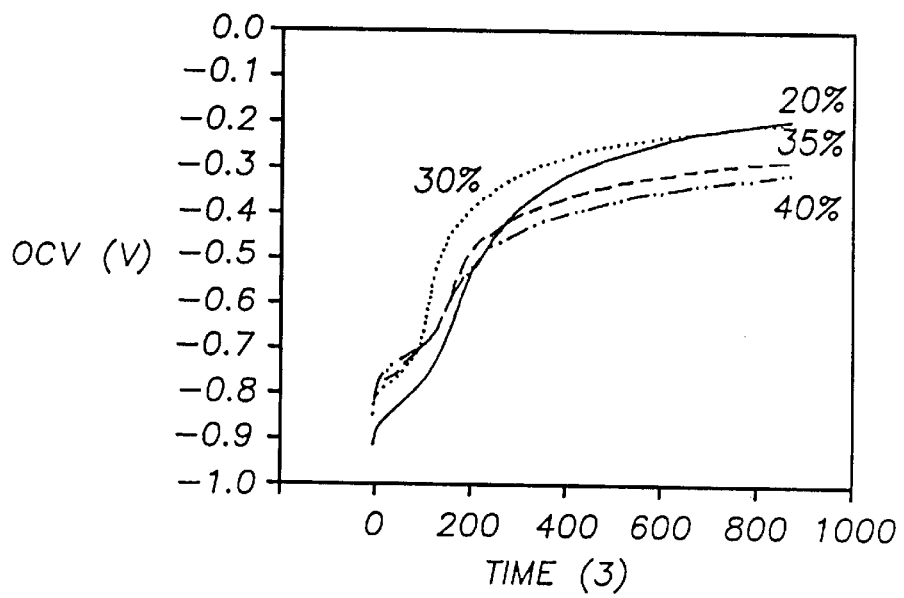
FIG. 15 is a plot of OCV recovery curves for the I-V potential sweeps shown in FIG. 14.

The OCV recovery curves (FIG. 15) for the i-V sweeps in FIG. 14 reveal more information about the system. The OCV remains approximately the same for several minutes at a potential close to 0.8 V. During this time the Fe formed during the i-V sweep is being reoxidized by the slowly equilibrating slag. When the electrolytically formed iron has been reoxidized, the $Fe^{3+}/Fe^{2+}$ equilibrium will determine the potential, causing a quick relaxation to less negative potentials. Finally, after approximately 15 minutes, the slag acquires a stable potential which describes the new oxygen activity of the entire slag. The slag has changed its oxygen content because oxygen has been removed from the slag through the PSZ. There is a difference in the level of the intermediate plateau on the OCV plots for the recovery of slags of different concentrations of $Fe_2O_3$. This difference is indicative of a greater activity of FeO near the slag/PSZ interface in the slags with higher $Fe_2O_3$ initial concentration.

Figure 16:
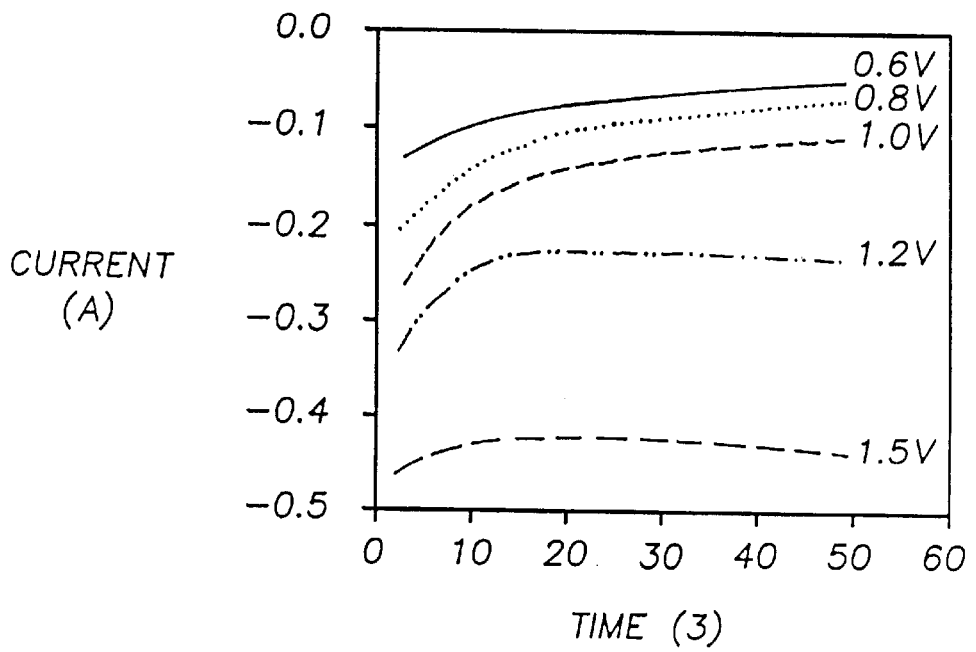
FIG. 16 are current-time profiles for potentiostatic measurements.
Figure 17:
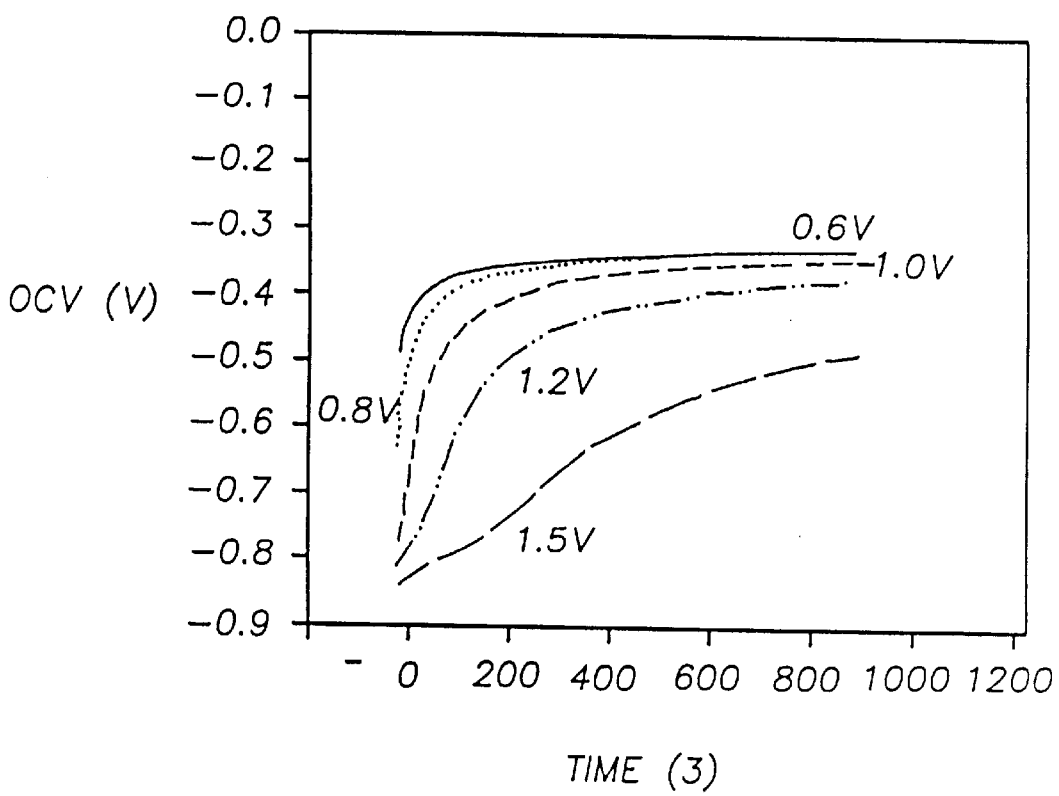
FIG. 17 are OCV recovery profiles for the potentiostatic measurements in FIG. 16.

The potentiostatic curves (FIG. 16) which were run at different potentials along the i-V plot provides further proof for the reactions occurring during the i-V sweep (FIG. 14). The potentiostatic curves yielded approximately constant currents after long times (50 sec) which corresponded well to the plateau and edge levels generated during the sweep. The potentiostatic curves which are at potentials corresponding to the edge (<-1V) of the i-V sweep demonstrate a flat region corresponding to Fe in their OCV recovery curves (FIG. 17) and also demonstrate significantly larger currents (FIG. 16). These details further reinforce the theory that the FeO dissociation is occurring at the edge and $Fe_3O_3$ dissociation is occurring along the plateau of the i-V curves.

Figure 18:
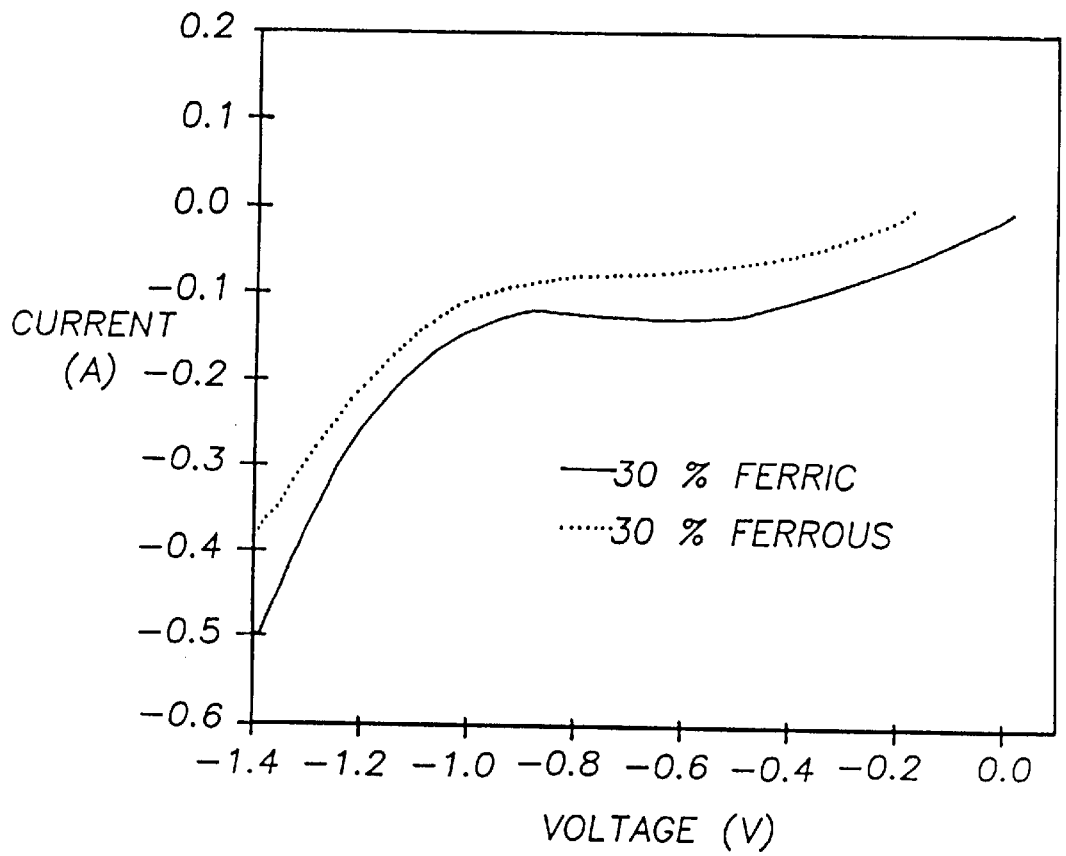
FIG. 18 is a plot of i-V curves for two slags with the same iron oxide concentration and different oxygen activities.
Figure 19:
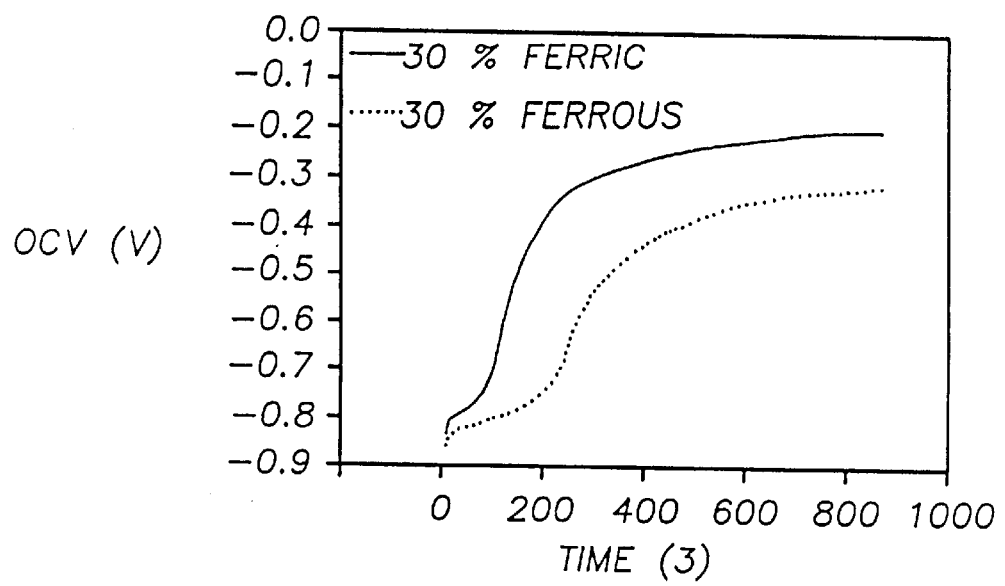
FIG. 19 is a plot of the OCV recovery curves for the i-V plots shown in FIG. 18.

The i-V curves for two slags of different initial oxygen activities but same overall iron concentration are shown in FIG. 18. The initial type I OCV difference was determined by the $Fe^{3+}/Fe^{2+}$ ratio in the slag. The reduced oxygen activity in the slag with the higher FeO content was detected by the initial open-circuit value. As expected, the plateau in the i-V curve demonstrated lower current in comparison with the other slag because of the lower initial concentration of $Fe_2O_3$. The OCV recovery curves are shown for both slags in FIG. 19.

EXAMPLE 3

This example demonstrates a type II measurement on an alumina-free slag. The setup was similar to the cell described in Example 2 and FIG. 9. Such slags are very corrosive to alumina and therefore the shielding tube 124 was not immersed into the melt.

A synthetic slag containing 30 wt % $Fe_2O_3$ was used. This slag was found to be relatively non-corrosive with respect to the PSZ. The slag was prepared by milling CaO, $SiO_2$, and $Fe_2O_3$ powders (Alfa-Aesar) in the appropriate proportions with isopropyl alcohol for 24 hours. The powder mixtures were then pressed into pellets. The pellets were sintered in air at 1000° C. for 6 hours. The resulting pellets were crushed and melted in the cell.

The cell was heated at 4°/min to 1510° C. (1783 K), the slag was allowed to equilibrate for 15 min. During equilibration, the WE and RE2 assembly was located at 2.54 cm (1") above the slag. The WE ad RE2 were then immersed into the slag and a 10 minute type I open circuit measurement (OCV) was taken to determine the oxygen activity. Thereafter, a type II −0.3 V applied potential step was applied to the circuit for 90 seconds. This was immediately followed by a 10 minute type I open circuit recovery measurement. Another type II −0.3 V applied potential step was applied to the circuit for 90 seconds. This was immediately followed by a 10 minute type I open circuit recovery measurement. Finally, a type II −0.5 V applied potential step was applied to the circuit for 90 seconds. This was immediately followed by a 10 minute type I open circuit recovery measurement. All potential measurements were taken with respect to RE1.

Figure 20:
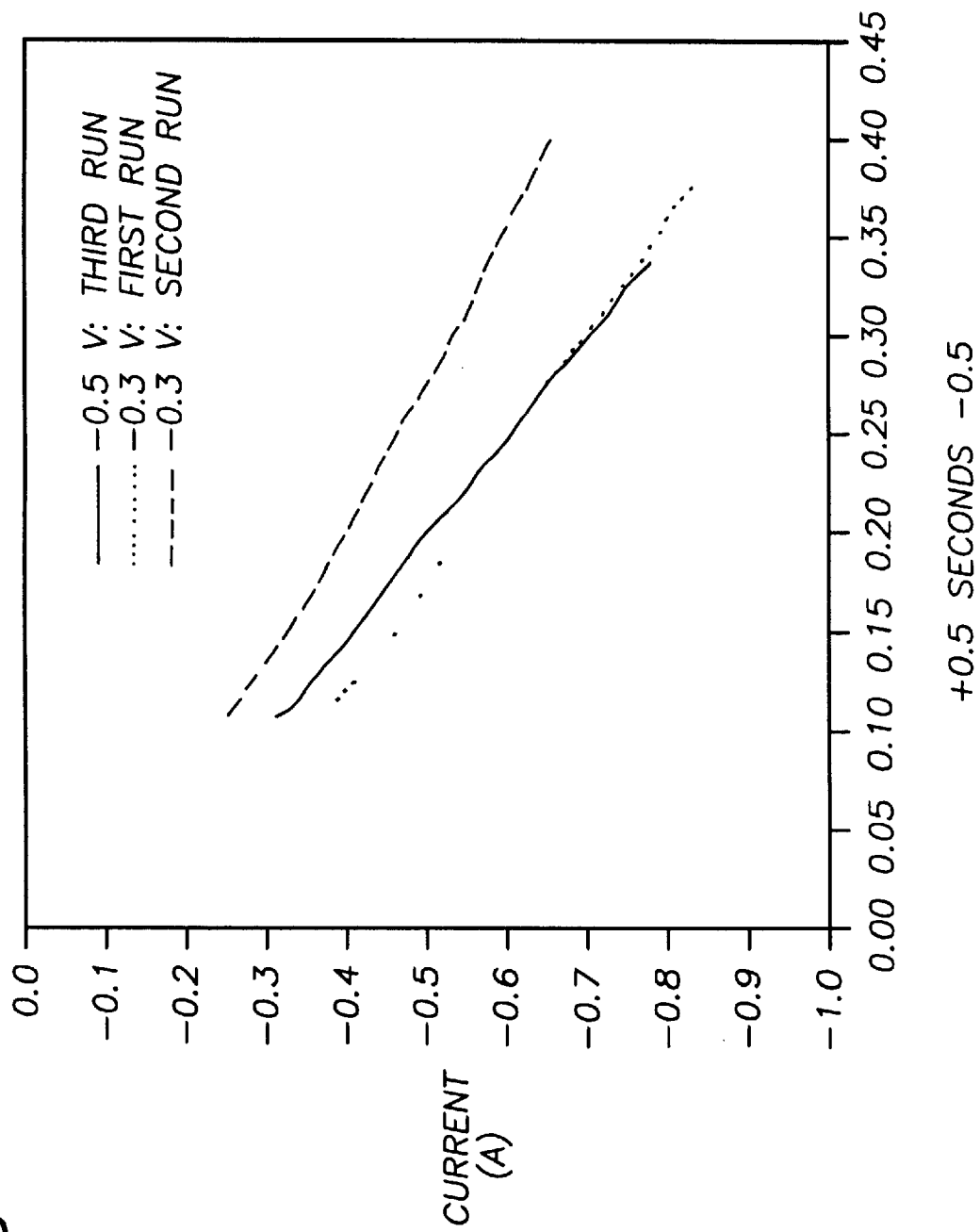
FIG. 20 is a plot of current-time response to an applied potential step.

The resulting current-time profiles of the three applied potential steps are shown in FIG. 20. The current-time response was found to be linear, supporting the hypothesis that the rate limiting transport process is diffusion polarization at the working electrode.

EXAMPLE 4

This example present the analysis of slags with various iron oxide concentrations using Type III measurements.

The experimental cell for this example is shown in FIG. 10 and is similar to the apparatus described above in Example 2. Six additional 1" Pt wires were welded to the RE2-WE internal electrode in order to significantly increase the surface are to volume ratio. Instead of utilizing a Solartron 1287 potentiostat, a Hewlett-Packard 6033A power source was used to drive current across the CE and WE while the potential was monitored across RE1 and RE2 using a digital voltmeter. The power source was utilized because it had higher output current capability than the Solatron 1287 potentiostat. The slag used in this experiment was identical to the slag used in Example 2.

The cell was heated at 4°/min up to 1525° C. (1800 K) and the slag was allowed to equilibrate for 15 minutes. During equilibration, the WE and RE2 assembly was located 2.54 cm (1 inch) above the slag. The WE and RE2 were then immersed into the slag and a 10 minute type I open circuit measurement (OCV) was taken in order to determine the oxygen activity. The potential of RE2 was then ramped from the OCV to −0.5 V relative to the RE1 over a period of 10 minutes and the resulting current was measured using a current probe. The potential of RE2 was then increased gradually to −1.0 V relative to the RE1 over a period of 10 minutes and the resulting current was again measured. The cell was then quenched and sectioned.

Table 2 summarizes the results found during the type III electrolysis measurements performed in group C. The total charge ($Q_{Fe2O3}$) associated with the reduction of the ferric to the ferrous oxide was approximately 70% of the predicted value. A combination of three possible reasons would account for this difference: a) degassing of oxygen from the slag into the argon shielding gas prior to taking the electrolysis measurement; b) application of −0.5 V does not provide a strong enough driving force for the complete removal of all the $Fe_2O_3$ from the slag; c) in locations far from the WE-RE2 electrodes residual amounts of $Fe_2O_3$ remain in the slag which cannot be reduced.

TABLE 2

Type III Electrolysis Measurement Results

| Species Electrolyzed | Applied Potential (Volts) | Predicted Charge (Coulombs) | Realized Charge (Coulombs) | % of Predicted Charge Realized | wt % of FeO remaining |
|---|---|---|---|---|---|
| $Fe_2O_3$ | −0.5 | 544 | 371 | 68 | NA |
| FeO | −1.0 | 1088 | 1121 | 103 | NA |

TABLE 2-continued

Type III Electrolysis Measurement Results

| Species Electrolyzed | Applied Potential (Volts) | Predicted Charge (Coulombs) | Realized Charge (Coulombs) | % of Predicted Charge Realized | wt % of FeO remaining |
|---|---|---|---|---|---|
| Total Fe containing species | −1.0 | 1632 | 1492 | 91.5 | 4.7 |

The total charge ($Q_{FeO}$) associated with the reduction of ferrous oxide to electrolytic iron was 103% of the predicted value. This larger than expected difference is likely to have been caused by residual ferric species which were not fully reduced during the initial electrolysis.

The total charge ($Q_{FeO}$) associated with the reduction of ferrous oxide to electrolytic iron was approximately 91.5% of the predicted value. Assuming any iron oxide remaining is in the ferrous state, this would indicate that the residual FeO remaining in the slag would be about 4.7 wt %. The significant change in slag color was indicative of a lower iron oxide content. Iron dendrites were found adjacent to the platinum wires.

What is claimed is:

1. A system for electrolytic extraction of a metal at temperatures of greater than 1000° C., comprising;
    a vessel containing a metal oxide electrolyte, wherein the metal oxide, at a temperature of greater than 1000° C., is a solvent for a metallic species to be extracted and an anionic species;
    an anion-conducting membrane in contact with the metal oxide electrolyte;
    a cathode in electrical contact with the metal oxide electrolyte;
    an anode separated from the metal oxide electrolyte by the anion-conducting membrane; and
    means for establishing a potential difference between the cathode and the anode.

2. The apparatus of claim 1, wherein the anion-conducting membrane comprises:
    a primary membrane in contact with the metal oxide electrolyte; and
    means for inhibiting electronic conductance.

3. The apparatus of claim 2, wherein said inhibiting means comprises a secondary membrane adjacent to the primary membrane, said secondary membrane having substantially only ionic conducting characteristics.

4. The apparatus of claim 1, wherein said cathode possesses a large area for providing large cathode-electrolyte contact area.

5. The apparatus of claim 1, further comprising stirring means.

6. The apparatus of claim 1, wherein the metal oxide electrolyte comprises basic oxides.

7. The apparatus of claim 1, wherein the metal oxide electrolyte is a solvent for a metallic species to be extracted and an anionic species at a temperature in the range of greater than 1000° C. to about 1600° C.

8. The apparatus of claim 1, wherein the anion-conducting membrane comprises a solid electrolyte.

9. The apparatus of claim 1, wherein the anion-conducting membrane comprises a liquid electrolyte.

10. The apparatus of claim 9, wherein the liquid electrolyte comprises $CaAlSiFeO_x$, where x is selected to provide a metal oxide with high oxygen conductivity and electronic conductivity corresponding to an electronic transport number of less than 0.1 at operating temperatures.

11. The apparatus of claim 1, wherein at least a portion of the vessel comprises the anion-conducting membrane.

12. The apparatus of claim 1, wherein the vessel is comprised of the anion-conducting membrane.

13. The apparatus of claim 1, wherein the metal oxide electrolyte comprises metal oxide slag.

14. The apparatus of claim 1, wherein the means for applying a potential is selected to apply a potential that electrolytically reduces a single metallic species to the corresponding metal.

15. The apparatus of claim 1, wherein the means for applying a potential is selected to apply a potential that simultaneously reduces a plurality of metallic species.

16. The apparatus of claim 1, wherein the cathode is selected from the group consisting of inert metal and plasma arc electrodes.

17. The apparatus of claim 1, wherein the vessel is equipped with a plurality of cathodes and anodes, each having means for independently applying a potential.

18. The apparatus of claim 1, wherein the vessel comprises a plurality of cathodes.

19. The apparatus of claim 1, wherein the metal oxide electrolyte is a solvent for a metallic species to be extracted and an anionic species at a temperature in the range of about 1200° C. to about 1600° C.

20. The apparatus of claim 1, wherein the cathode comprises a ceramic/metal composite electrode.

21. A composite ionic membrane for use in an electrolytic cell, comprising:
    a first oxygen anion-conducting membrane; and
    a second oxygen anion-conducting membrane having an electronic transport of less than 0.1 in contact with the first oxygen anion-conducting membrane for inhibiting electronic conduction through the composite membrane.

22. An apparatus for extraction of metal from a molten electrolyte, comprising:
    a vessel for holding and maintaining a metal oxide electrolyte at a preselected temperature;
    a cathode in electrical contact with the metal oxide electrolyte;
    an anode separated from the cathode and the metal oxide electrolyte by an anion-conducting membrane;
    means for establishing a potential between the cathode and the anode;
    a first reference electrode in electrical contact with both the cathode and the metal oxide electrolyte to measure a potential at the metal oxide electrolyte-cathode interface;
    a second reference electrode positioned in electrical contact with the anion-conducting membrane and a reference gas to serve as a reference electrode indicative of the potential at the membrane-reference gas interface; and
    means for measuring a potential between the first and second reference electrode.

* * * * *